United States Patent
Qian et al.

(10) Patent No.: US 11,429,247 B1
(45) Date of Patent: Aug. 30, 2022

(54) INTERACTIONS WITH SLICES OF MEDICAL DATA IN AUGMENTED REALITY

(71) Applicant: Medivis, Inc., New York, NY (US)

(72) Inventors: Long Qian, Brooklyn, NY (US); Christopher Morley, New York, NY (US); Osamah Choudhry, New York, NY (US); Alfred Yu-chih Tarng, San Jose, CA (US)

(73) Assignee: Medivis, Inc., New York, NY (US)

( * ) Notice: Subject to any disclaimer, the term of this patent is extended or adjusted under 35 U.S.C. 154(b) by 0 days.

(21) Appl. No.: 17/502,037

(22) Filed: Oct. 14, 2021

Related U.S. Application Data

(63) Continuation-in-part of application No. 17/395,233, filed on Aug. 5, 2021, and a continuation-in-part of application No. 17/194,191, filed on Mar. 5, 2021, now Pat. No. 11,307,653.

(51) Int. Cl.
  *G06T 19/00* (2011.01)
  *G06F 3/04815* (2022.01)
  *G06F 3/01* (2006.01)
  *G06F 3/0482* (2013.01)

(52) U.S. Cl.
  CPC .......... *G06F 3/04815* (2013.01); *G06F 3/011* (2013.01); *G06F 3/017* (2013.01); *G06F 3/0482* (2013.01); *G06T 19/006* (2013.01); *G06T 2210/41* (2013.01)

(58) Field of Classification Search
  None
  See application file for complete search history.

(56) References Cited

U.S. PATENT DOCUMENTS

| | | |
|---|---|---|
| 10,872,460 B1 | 12/2020 | Luo et al. |
| 2008/0228064 A1 | 9/2008 | Krueger et al. |
| 2010/0002921 A1 | 1/2010 | Fenchel et al. |
| 2018/0193097 A1 | 7/2018 | Mclachlin et al. |
| 2018/0253856 A1 | 9/2018 | Price et al. |
| 2020/0005486 A1 | 1/2020 | Sinha et al. |
| 2020/0054398 A1* | 2/2020 | Kovtun .................. G16H 40/63 |
| 2020/0352655 A1 | 11/2020 | Freese |
| 2021/0166486 A1 | 6/2021 | Kim et al. |

* cited by examiner

*Primary Examiner* — Nicholas R Wilson
(74) *Attorney, Agent, or Firm* — Cognition IP, P.C.; Edward Steakley; Rajesh Fotedar

(57) ABSTRACT

Various embodiments of an apparatus, methods, systems and computer program products described herein are directed to an Interaction Engine. The Interaction Engine generates, within a unified three-dimensional (3D) coordinate space: (i) a 3D virtual medical model positioned according to a model pose and (ii) at least one 3D virtual slice that corresponds with a view of respective slice layer from a plurality of slice layers associated with the 3D virtual medical model. The Interaction Engine renders an Augmented Reality (AR) display that includes concurrent display of the 3D virtual medical model and the 3D virtual slice(s). The Interaction Engine detects one or more physical gestures associated with the user and the physical instrument. The Interaction Engine identifies at least one interaction associated with the detected physical gestures and modifies the AR display according to the identified interaction.

20 Claims, 35 Drawing Sheets

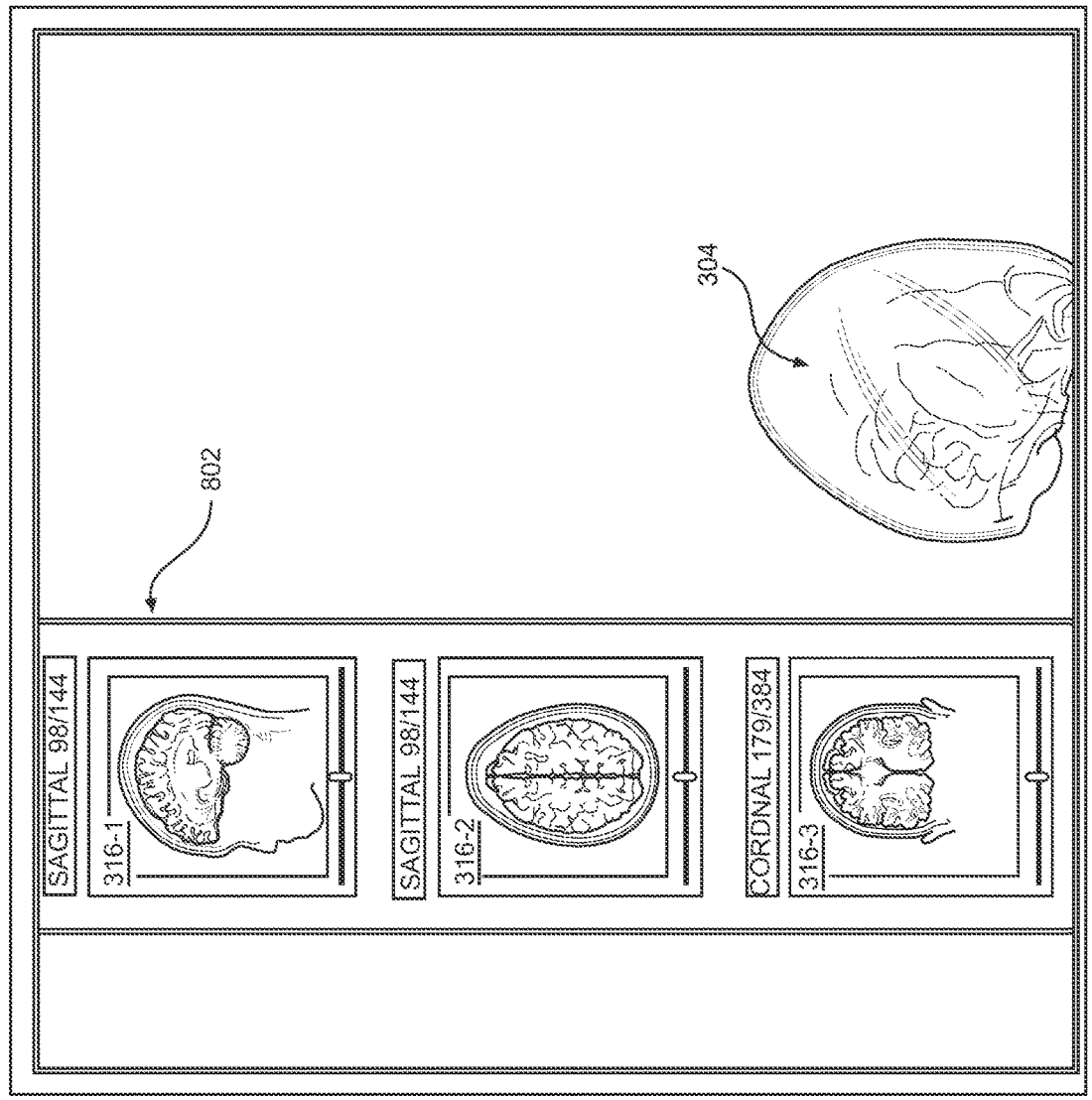

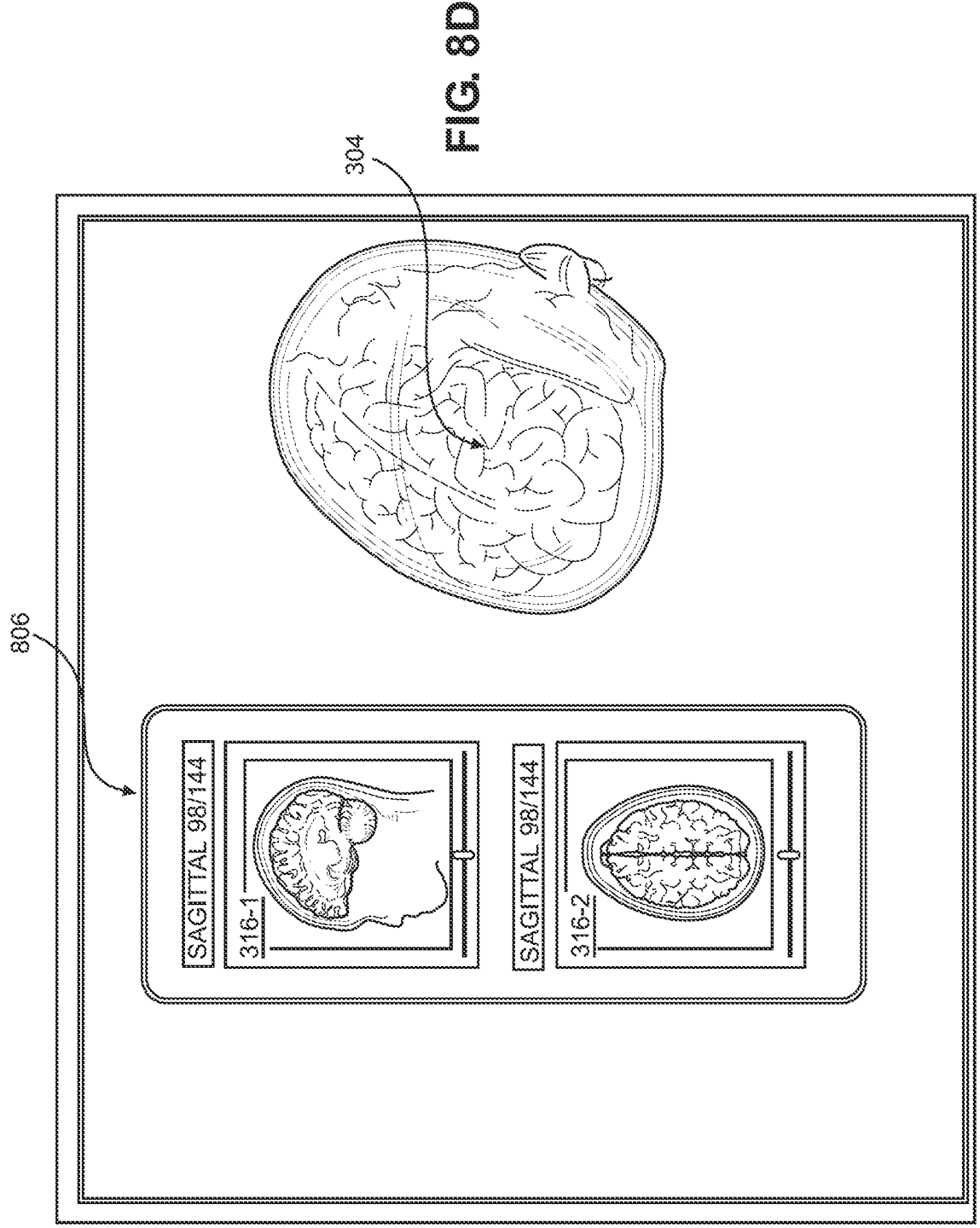

INTERACTIONS WITH SLICES OF MEDICAL DATA IN AUGMENTED REALITY

CROSS REFERENCE TO RELATED APPLICATIONS

This application is a continuation-in-part of U.S. patent application Ser. No. 17/194,191 entitled "User Input and Interface Design in Augmented Reality for Use in Surgical Settings," filed on Mar. 5, 2021, the entirety of which is incorporated by reference.

This application is a continuation-in-part of U.S. patent application Ser. No. 17/395,233 entitled "Physical Instrument with Fiducial Markers," filed on Aug. 5, 2021, the entirety of which is incorporated by reference.

BACKGROUND

Conventional systems provide for the rendering of virtual reality and augmented reality environments. Such environments provide a visualization of various portions of the physical world as well as simulations of certain events that will or may occur in the physical world. These conventional systems include communication with input devices controlled by one or more users. The input devices allow the users to select certain types of actions and activities within the rendered environments. In many cases, these environments rendered by conventional systems may be specific to certain types of industries. For example, some conventional virtual reality environments may be used to simulate training situations for a type of worker with duties specific to an occupation. In another example, some conventional virtual reality environments may be used to model future events and visualize the occurrence and effects of the modeled future events on a particular physical geographical location.

SUMMARY

Conventional systems for three-dimensional (3D) visualization lack a certain types of functionalities that allow a user(s) to interact and manipulate rendered objects by physical gestures. Various embodiments of the Interaction Engine described herein provide significant improvements of the limitations of conventional systems by providing and implementing various types of virtual interactions. The Interaction Engine tracks a user's movements in the physical world and/or physical instrument's movements represents such movements as virtual interactions rendered within a unified 3D coordinate space. Such virtual interactions may result in movement and manipulation of rendered objects in a 3D display. Such virtual interactions may further result in changes to display positions of the rendered objects that trigger portrayal in the 3D display of different types of visual data.

Various embodiments of an apparatus, methods, systems and computer program products described herein are directed to an Interaction Engine. The Interaction Engine generates, within a unified three-dimensional (3D) coordinate space: (i) a 3D virtual medical model positioned according to a model pose and (ii) at least one 3D virtual slice that corresponds with a view of respective slice layer from a plurality of slice layers associated with the 3D virtual medical model. The Interaction Engine renders an Augmented Reality (AR) display that includes concurrent display of the 3D virtual medical model and the 3D virtual slice. The Interaction Engine detects one or more physical gestures of the user and physical instruments. The Interaction Engine identifies at least one virtual interaction associated with the detected physical gestures and modifies the AR display according to the identified virtual interaction.

According to various embodiments, the Interaction Engine may implement a slice panel control virtual interaction. The slice panel control virtual interaction includes one or more of selection of a slice panel hide button, selection of a slice panel anchor button, selection of a slice panel layout button and selection of a slice close button.

According to various embodiments, the Interaction Engine may implement a two-dimensional (2D) display of slices on a display screen(s) of one or more computer systems. The Interaction Engine may implement a slice enlargement interaction, a slice zoom-interaction, a slice scroll interaction, and a slice move interaction for the 2D display of the slices.

According to various embodiments, the Interaction Engine may include an axis mode and an inline mode. In axis mode, a slice(s) is based on medical model data that correspond to coordinates the line on a plane that is parallel to an original axis of the 3D medical dataset (CT, MRI etc). In inline mode, a slice(s) is not restricted to the original axis of the 3D medical dataset.

According to various embodiments, the Interaction Engine may implement a 3D slice activation and de-activation virtual interaction. The 3D slice activation virtual interaction includes one or more of: activation of a 3D virtual slice menu and display of 3D virtual slice panel that consists of multiple slices.

According to various embodiments, the Interaction Engine may implement a slice panel manipulation virtual interaction. The slice panel manipulation virtual interaction includes selection of one or more of: enlargement, zoom-in and zoom-out, move and rotate. In one or more embodiments, the slice panel manipulation virtual interaction may be performed with user hand gestures.

According to various embodiments, the Interaction Engine may implement a slice layer selection virtual interaction while the axis mode is active. The slice layer selection virtual interaction includes one or more of: selection of a slice button and selection of a slice scroll-bar.

According to various embodiments, the Interaction Engine may implement an instrument virtual interaction.

According to various embodiments, the Interaction Engine may implement a trajectory virtual interaction. The trajectory virtual interaction includes a trajectory focus virtual interaction.

According to various embodiments, the Interaction Engine may implement a slice freeze virtual interaction while the axis mode is active or the inline mode is active.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein:

FIGS. 8A, 8B, 8C and 8D are each a diagram illustrating an exemplary environment in which some embodiments may operate.

DETAILED DESCRIPTION

Figure 1A:
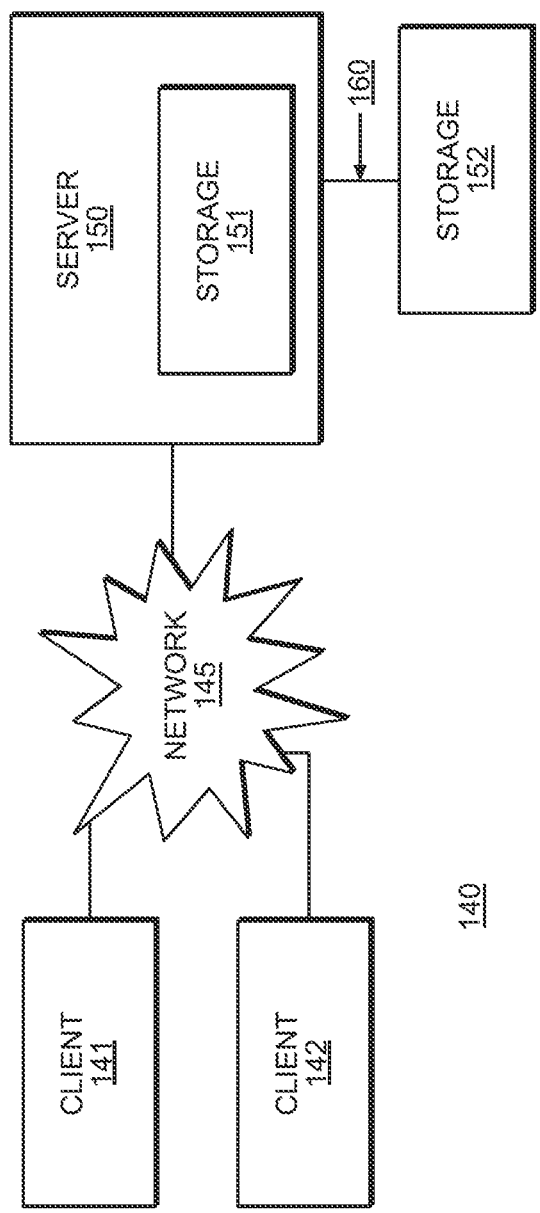
FIG. 1A is a diagram illustrating an exemplary environment in which some embodiments may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

A diagram of exemplary network environment in which embodiments may operate is shown in FIG. 1A. In the exemplary environment 140, two clients 141, 142 are connected over a network 145 to a server 150 having local storage 151. Clients and servers in this environment may be computers. Server 150 may be configured to handle requests from clients.

The exemplary environment 140 is illustrated with only two clients and one server for simplicity, though in practice there may be more or fewer clients and servers. The computers have been termed clients and servers, though clients can also play the role of servers and servers can also play the role of clients. In some embodiments, the clients 141, 142 may communicate with each other as well as the servers. Also, the server 150 may communicate with other servers.

The network 145 may be, for example, local area network (LAN), wide area network (WAN), telephone networks, wireless networks, intranets, the Internet, or combinations of networks. The server 150 may be connected to storage 152 over a connection medium 160, which may be a bus, crossbar, network, or other interconnect. Storage 152 may be implemented as a network of multiple storage devices, though it is illustrated as a single entity. Storage 152 may be a file system, disk, database, or other storage.

In an embodiment, the client 141 may perform the method 300 or other method herein and, as a result, store a file in the storage 152. This may be accomplished via communication over the network 145 between the client 141 and server 150. For example, the client may communicate a request to the server 150 to store a file with a specified name in the storage 152. The server 150 may respond to the request and store the file with the specified name in the storage 152. The file to be saved may exist on the client 141 or may already exist in the server's local storage 151. In another embodiment, the server 150 may respond to requests and store the file with a specified name in the storage 151. The file to be saved may exist on the client 141 or may exist in other storage accessible via the network such as storage 152, or even in storage on the client 142 (e.g., in a peer-to-peer system).

In accordance with the above discussion, embodiments can be used to store a file on local storage such as a disk or on a removable medium like a flash drive, CD-R, or DVD-R. Furthermore, embodiments may be used to store a file on an external storage device connected to a computer over a connection medium such as a bus, crossbar, network, or other interconnect. In addition, embodiments can be used to store a file on a remote server or on a storage device accessible to the remote server.

Furthermore, cloud computing is another example where files are often stored on remote servers or remote storage systems. Cloud computing refers to pooled network resources that can be quickly provisioned so as to allow for easy scalability. Cloud computing can be used to provide software-as-a-service, platform-as-a-service, infrastructure-as-a-service, and similar features. In a cloud computing environment, a user may store a file in the "cloud," which means that the file is stored on a remote network resource though the actual hardware storing the file may be opaque to the user.

Figure 1B:
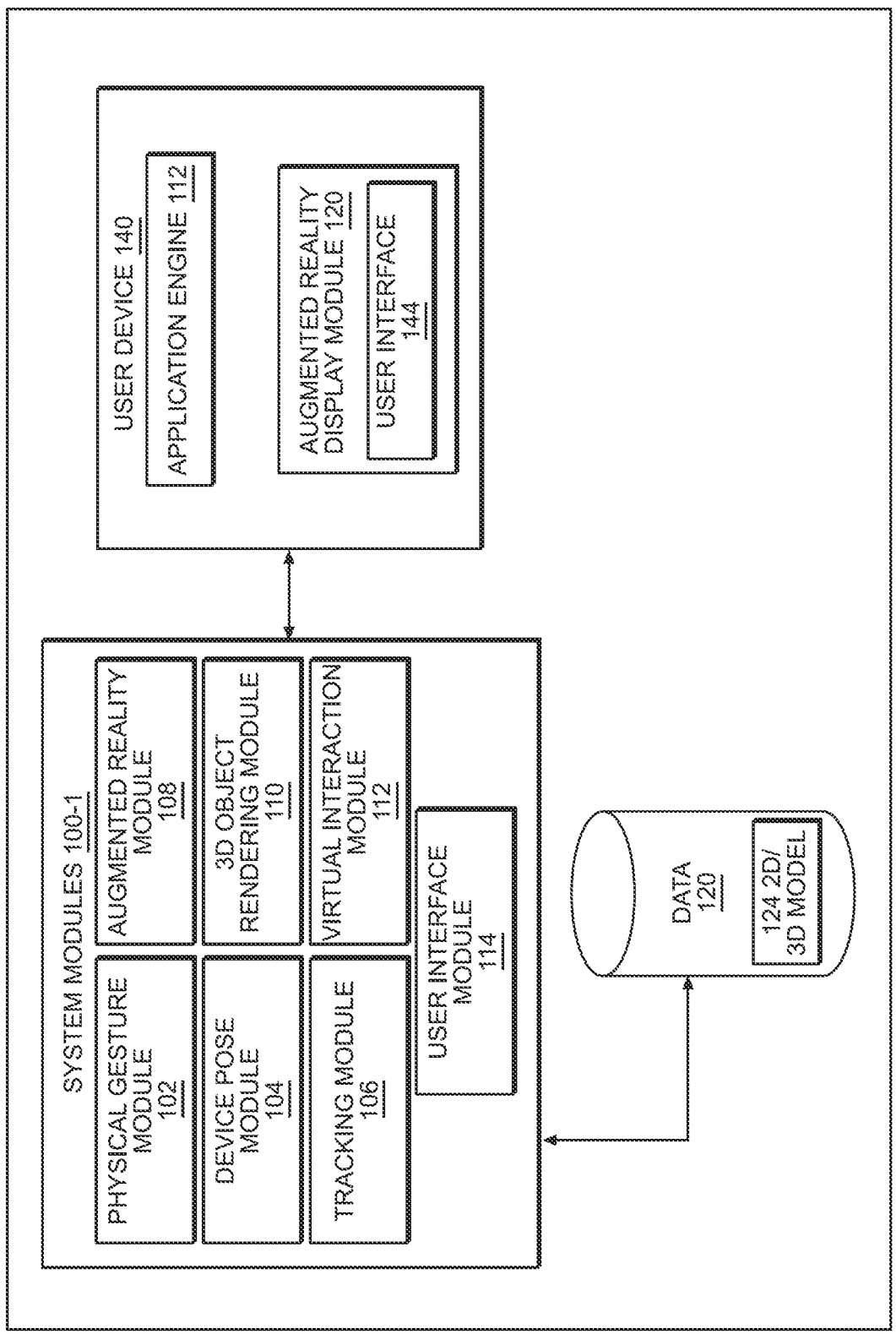
FIG. 1B is a diagram illustrating an exemplary environment in which some embodiments may operate.

FIG. 1B illustrates a block diagram of an example system 100 for an Interaction Engine that includes a physical gesture module 102, a device pose module 104, a tracking module 106, a an AR module 108, a 3D object rendering module 110, a virtual interaction module 112 and a user interface module 114. The system 100 may communicate with a user device 140 to display output, via a user interface 144 generated by an application engine 142. In various embodiments, the user device 140 may be an AR display headset device that further includes one or more of the respective modules 102, 104, 106, 108, 110, 112, 114.

The physical gesture module 102 of the system 100 may perform functionality, steps, operations, commands and/or instructions as illustrated in one or more of FIGS. 1C, 2A, 2B, 2C, 2D, 2E, 3A, 3B, 3C, 3D, 3E, 3F, 4, 5A, 5B, 6A, 6B, 7A, 7B, 8A, 8B, 8C, 8D, 9A, 9B, 9C, 9D, 9E, 9F, 9G, 10 and 11 ("FIGS. 1C-11").

The device pose module 104 of the system 100 may perform functionality, steps, operations, commands and/or instructions as illustrated in one or more of FIGS. 1C-11.

The tracking module 106 of the system 100 may perform functionality, steps, operations, commands and/or instructions as illustrated in one or more of FIGS. 1C-11.

The augmented reality module 108 of the system 100 may perform functionality, steps, operations, commands and/or instructions as illustrated in one or more of FIGS. 1C-11.

The 3D object rendering module 110 of the system 100 may perform functionality, steps, operations, commands and/or instructions as illustrated in one or more of FIGS. 1C-11.

The virtual interaction module 112 of the system 100 may perform functionality, steps, operations, commands and/or instructions as illustrated in one or more of FIGS. 1C-11.

The user interface module 114 of the system 100 may perform functionality, steps, operations, commands and/or instructions as illustrated in one or more of FIGS. 1C-11.

A database 120 associated with the system 100 maintains information, such as 3D medical model data 124, in a manner the promotes retrieval and storage efficiency and/or data security. In addition, the model data 124 may include rendering parameters, such as data based on selections and modifications to a 3D virtual representation of a medical model rendered for a previous Augmented Reality display. In various embodiments, one or more rendering parameters may be preloaded as a default value for our rendering parameter in a newly initiated session of the Interaction Engine.

In various embodiments, the Interaction Engine accesses one or more storage locations that contain respective portions of medical model data 124. The medical model data 124 may be represented according to two-dimensional (2D) and three-dimensional (3D) medical model data The 2D and/or 3D ("2D/3D") medical model data 124 may include a plurality of slice layers of medical data associated with external and internal anatomies. For example, the 2D/3D medical model data 124 may include a plurality of slice layers of medical data for generating renderings of external and internal anatomical regions of a user's head, brain and skull. It is understood that various embodiments may be directed to generating displays of any internal or external anatomical portions of the human body and/or animal bodies.

Figure 1C:
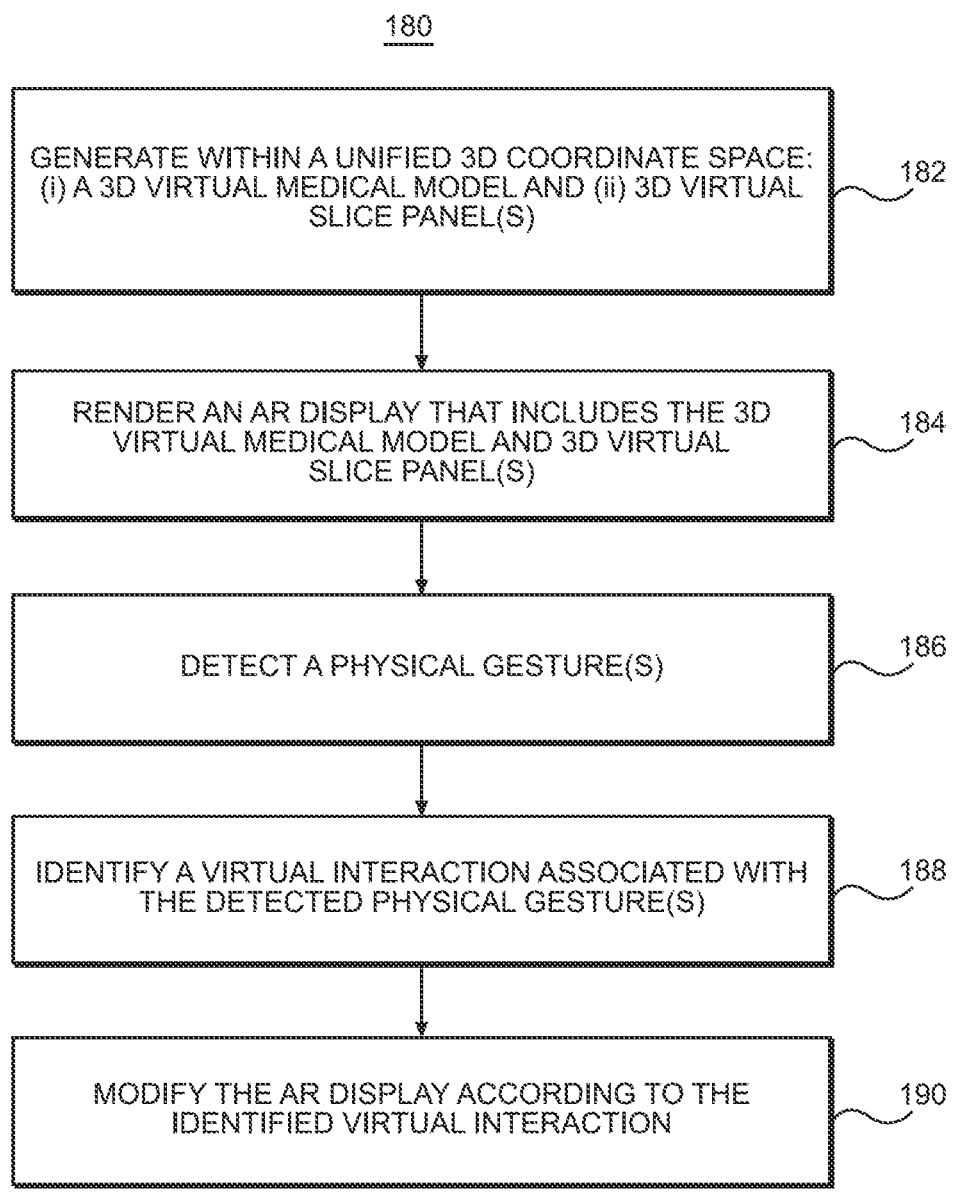
FIG. 1C is a diagram illustrating an exemplary method that may be performed in some embodiments.

As shown in the flowchart 180 of FIG. 1C, the Interaction Engine generates, within a unified three-dimensional (3D) coordinate space: a 3D virtual medical model positioned according to a model pose and at least one 3D virtual slice that corresponds with a view of respective slice layer from a plurality of slice layers associated with the 3D virtual medical model. (Act 182) The Interaction Engine renders an Augmented Reality (AR) display that includes concurrent display of the 3D virtual medical model and the 3D virtual slice(s). (Act 184) The Interaction Engine detects one or more physical gestures associated with the user and the physical instruments. (Act 186) The Interaction Engine identifies at least one virtual interaction associated with the detected physical gestures (Act 188) and modifies the AR display according to the identified virtual interaction. (Act 190).

Figure 2A:
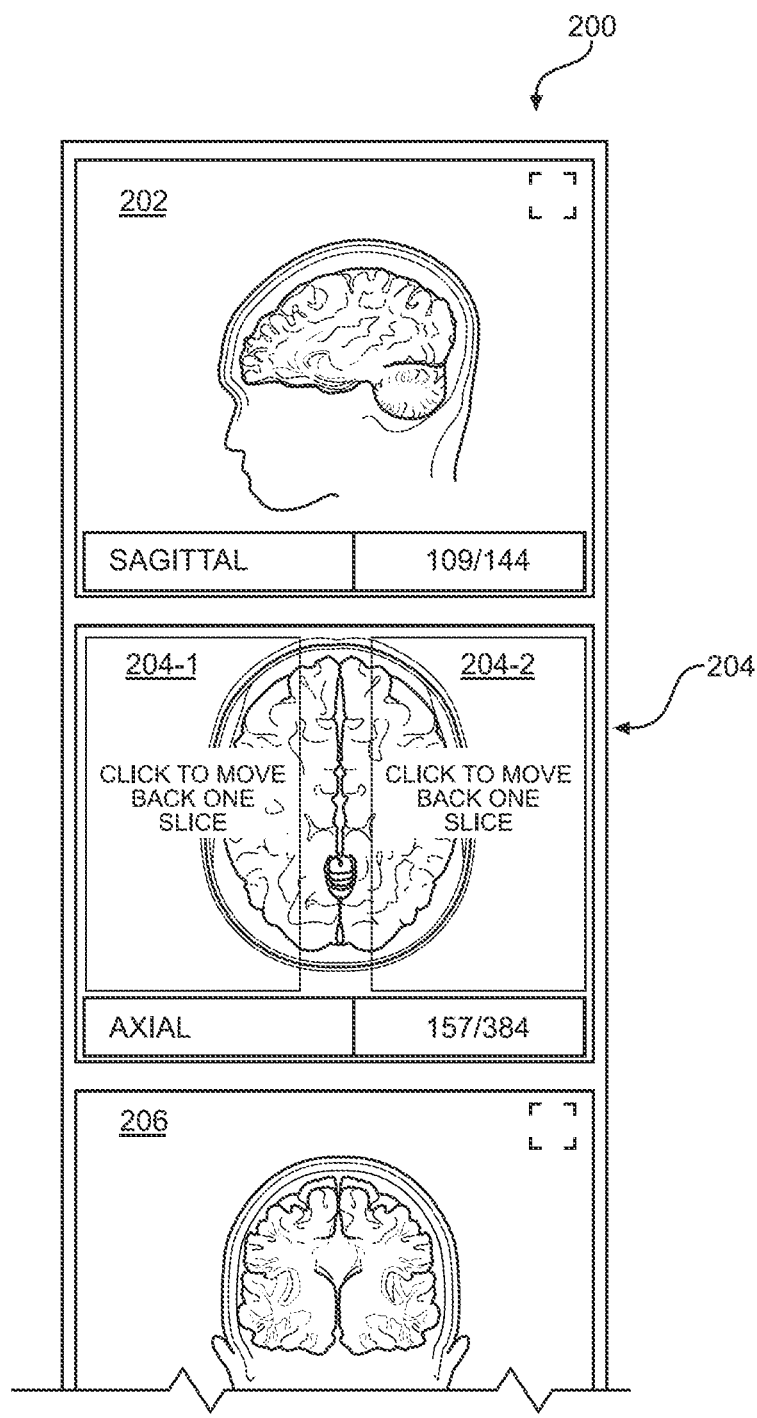
FIGS. 2A, 2B, 2C, 2D and 2E are each a diagram illustrating an exemplary environment in which some embodiments may operate.

As shown in FIG. 2A, the Interaction Engine may implement a two-dimensional (2D) display of slice (s)200 on a display screen(s) associated with one or more computer systems. The display 200 may include a plurality of slice views 202, 204, 206. For example, the display 200 may include a 2D virtual sagittal view 202 of a particular slice layer, a 2D virtual axial view 204 of another slice layer and a 2D virtual coronal view 206 of yet another different slice layer. It is understood that the respective slice layers portrayed in the 2D virtual slice views 202, 204, 206 represent various portions of 2D/3D medical model data and may further represent various different portions of 2D/3D medical model data.

In one or more embodiments, the Interaction Engine may implement 2D slice scroll buttons 204-1, 204-2. Upon detecting a selection of a respective slice scroll button 204-1, 204-2, the Interaction Engine modifies a slice indicator (such as slice layer number) that corresponds with various portions of 2D/3D medical model data. A first slice scroll button 204-1 may represent functionality for decrementing the current slice layer number. A second slice scroll button 204-2 may represent functionality for incrementing the current slice layer number. The Interaction Engine thereby updates the 2D virtual axial slice 204 to display the portions of 2D/3D medical model data that correspond with the modified slice layer number. It is understood that each of the 2D virtual slices 202, 204, 206 may have corresponding slice scroll buttons.

Figure 2B:
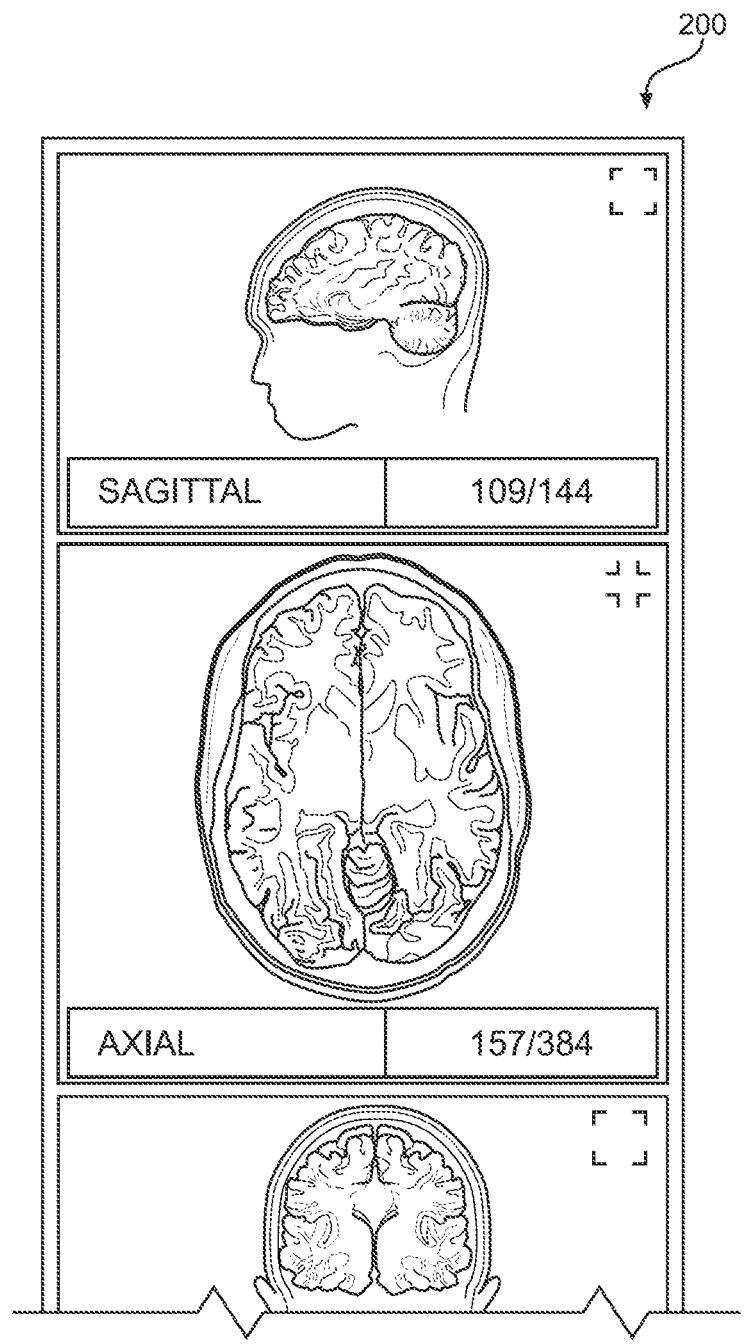

As shown in FIG. 2B, the Interaction Engine may receive a request to enlarge a particular slice. In response to the request, the Interaction Engine enlarges the particular slice. For example, the Interaction Engine renders an enlarged 2D virtual axial slice 208.

Figure 2C:
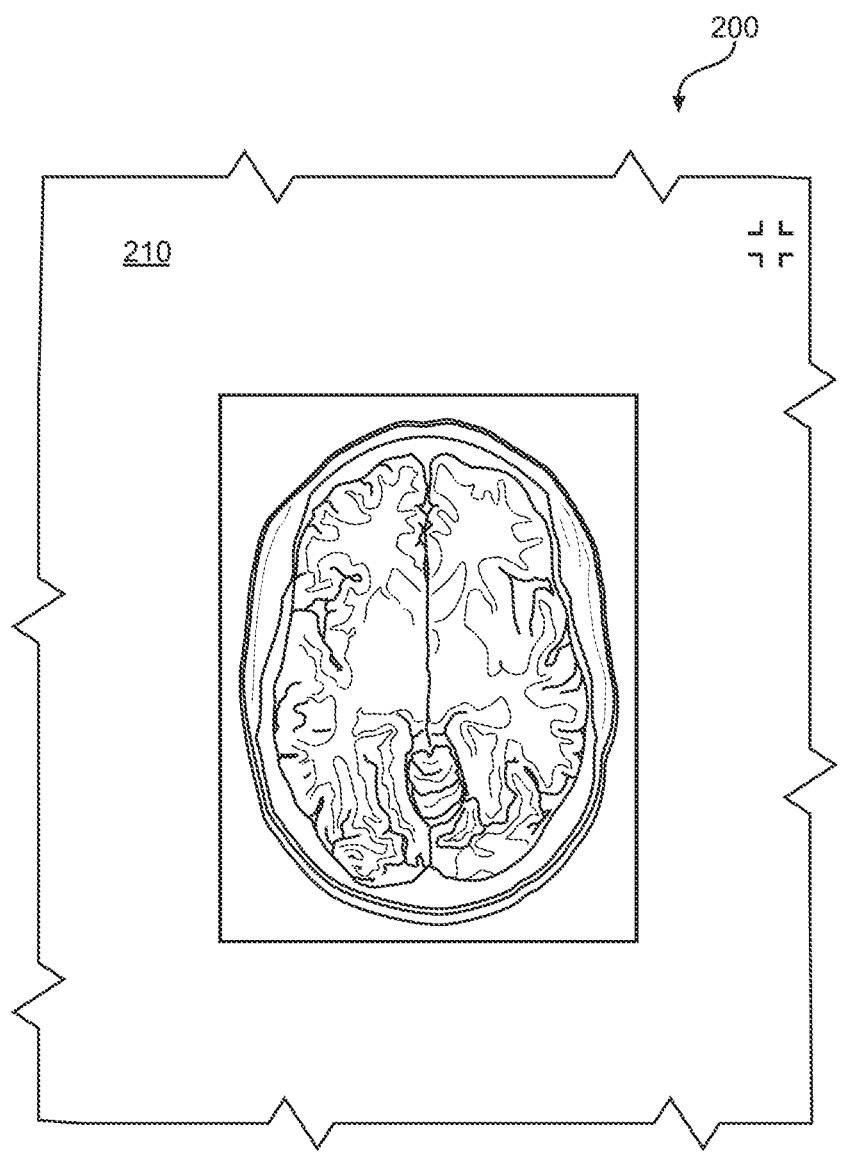
Figure 2D:
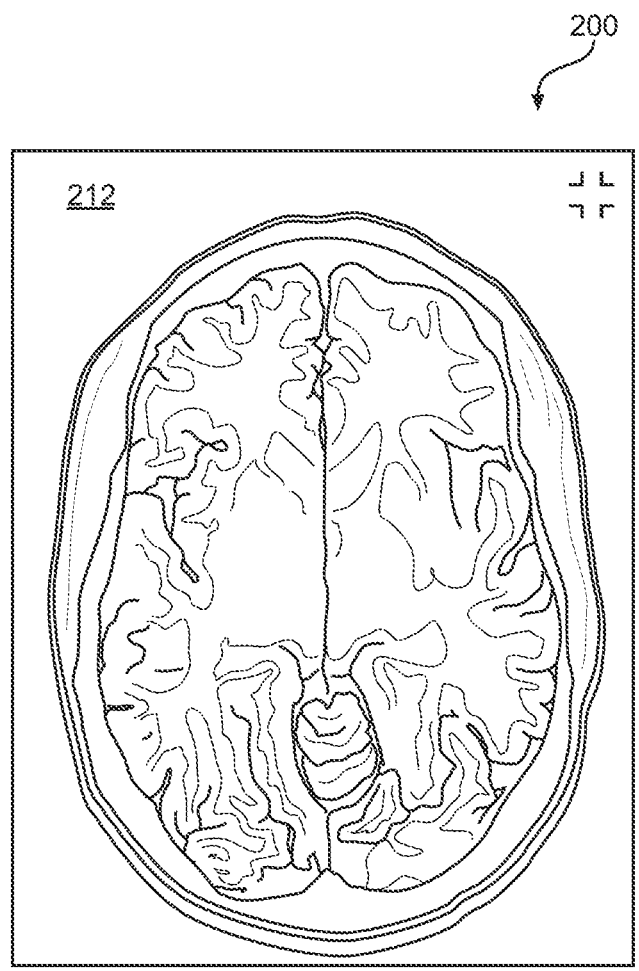
Figure 2E:
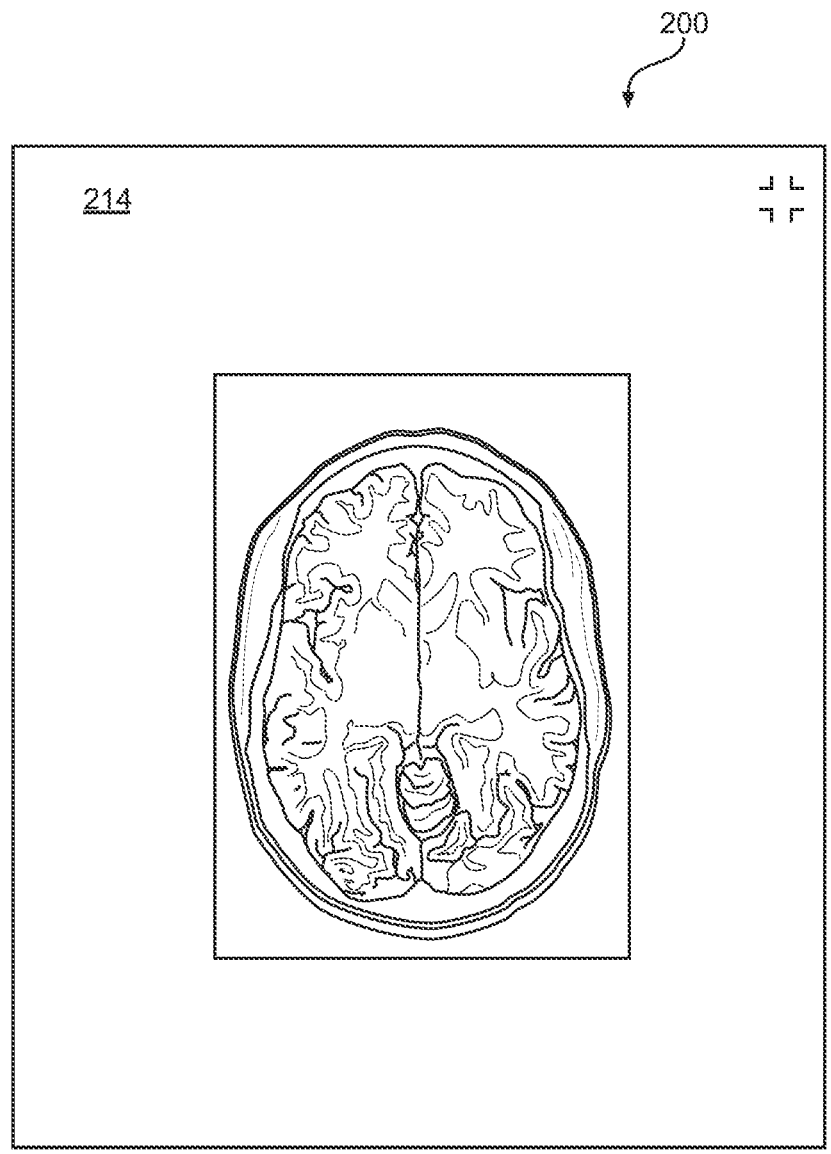

As shown in FIG. 2C, the Interaction Engine may render a further enlarged 2D virtual axial slice 210 in the display 200 in response to successive requests to further enlarge the 2D virtual axial slice 208. As shown in FIG. 2D, the Interaction Engine may implement a zoom-in virtual interaction on a particular 2D virtual slice 212. As shown in FIG. 2E, the Interaction Engine may implement a zoom-out virtual interaction on a particular 2D virtual slice 214. It is understood that the Interaction Engine may implement enlargement, zoom-in and zoom-out virtual interactions on each of the 2D virtual slices 202, 204, 206.

Figure 3A:
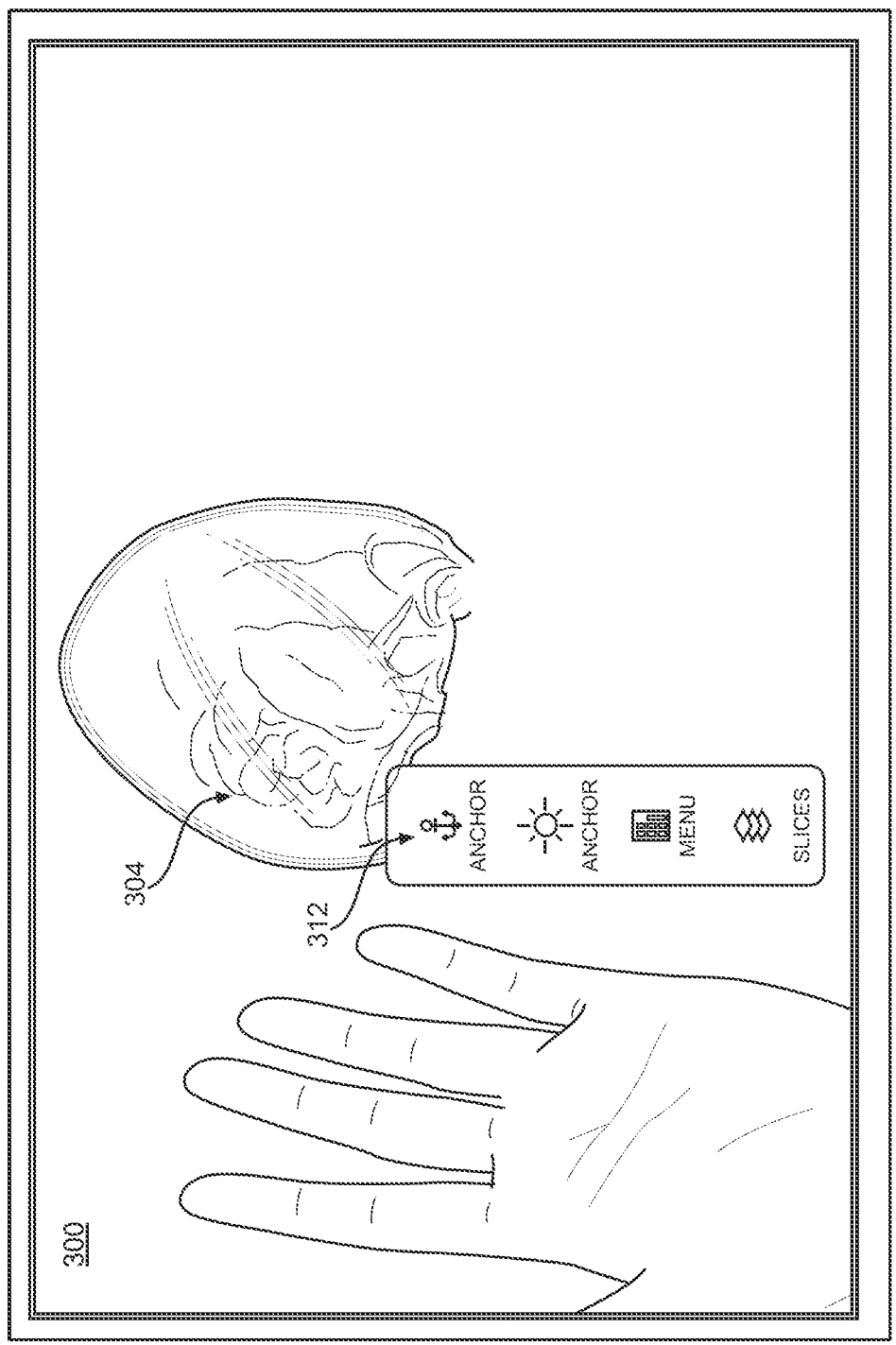
FIGS. 3A, 3B, 3C, 3D, 3E and 3F are each a diagram illustrating an exemplary environment in which some embodiments may operate.
Figure 3B:
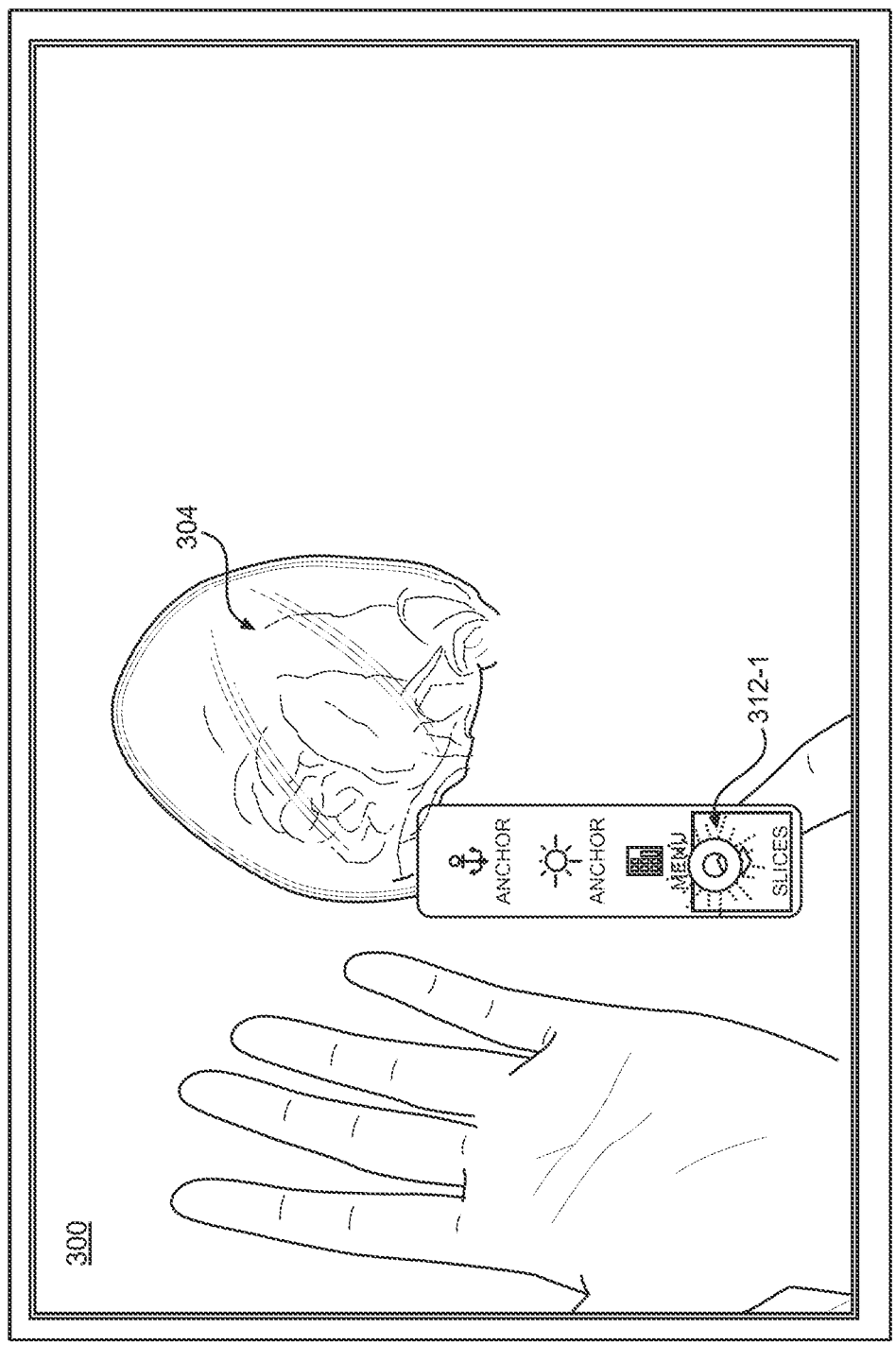
Figure 3C:
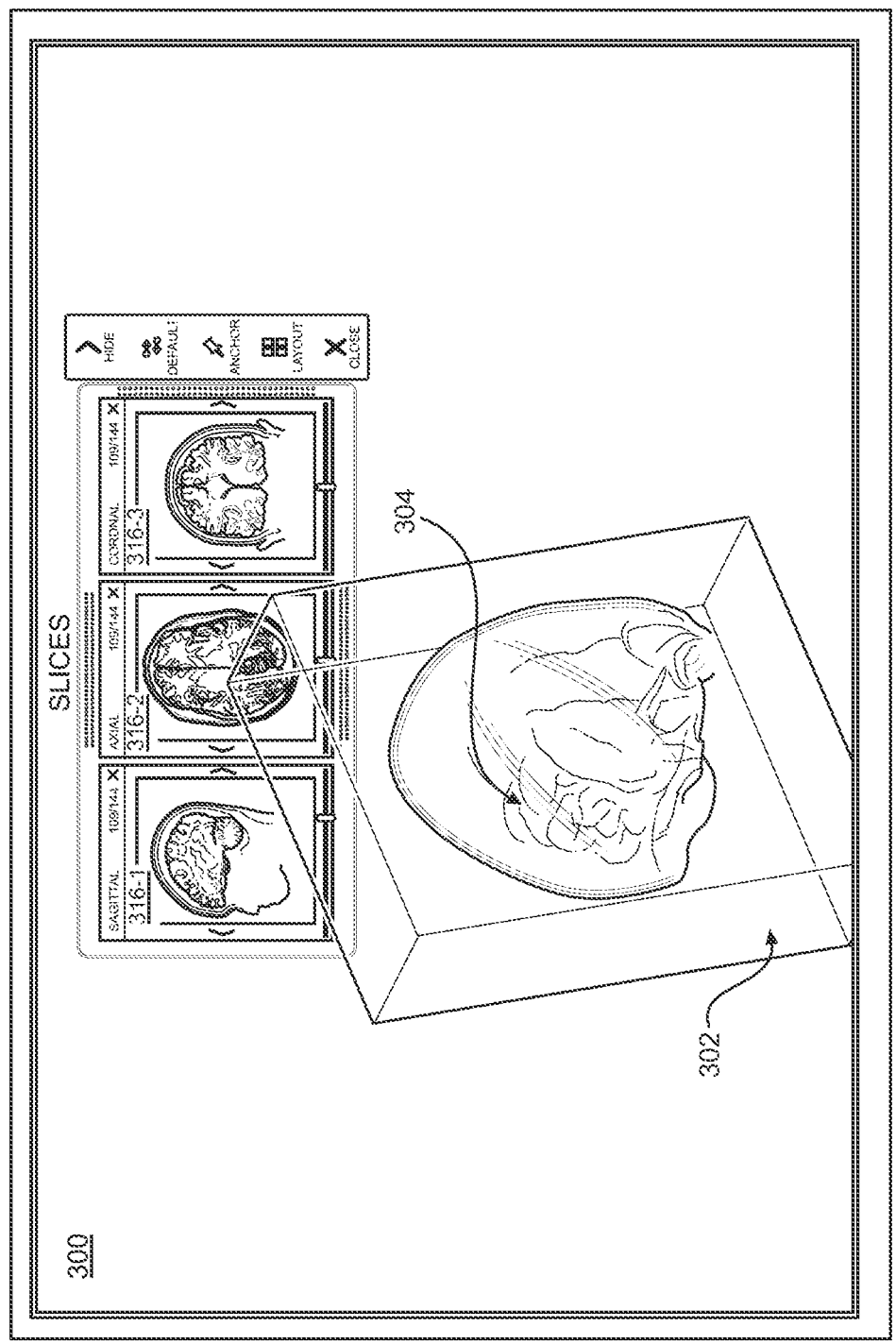

As shown in FIGS. 3A-3C, various embodiments of the Interaction Engine may implement a slice panel activation/de-activation virtual interaction. According to various embodiments, a user may wear an Augmented-Reality (AR) headset device that displays an AR display 300. The AR headset device may implement one or more modules of the Interaction Engine. The Interaction Engine generates an AR display 300, a 3D virtual representation of a medical model container 302 ("virtual container") and a 3D virtual representation of a medical model 304 ("3D virtual medical model"). The Interaction Engine further generates the AR display 300 to include display of one or more virtual components of a physical instrument. It is understood that the virtual container 302, the 3D virtual medical model 304 and the virtual components of the physical instrument, 3D virtual menus, 3D virtual selectable buttons, 3D virtual scroll-bars, 3D virtual panels and slices as described herein are various types of virtual objects generated by the Interaction Engine. Various types of selections and interactions may be applied to the virtual objects as described herein.

The Interaction Engine renders the medical model 304 in the AR display 300 based on the one or more portions of 3D medical model data, a model pose data and a current device pose data of the AR headset device. In addition, as shown in FIG. 3C, the Interaction Engine renders the 3D virtual medical model 304 in the virtual container 302 based on model pose data which describes an orientation and position of the rendering of the medical model 304. The Interaction Engine applies model pose data to the 3D medical model data to determine one or more positional coordinates in the unified 3D coordinate system for a portion(s) of medical model data associated with one or more medical model slice layers. The determined positional coordinates may further map to positional coordinates of a 3D interior space inside the virtual container 302.

The Interaction Engine further renders the 3D virtual medical model 304 based on the model pose data and a current device pose of an AR headset device worn by the user. The current device pose data represents a current position and orientation of the AR headset device in the physical world. The Interaction Engine translates the current device pose data to a position and orientation within the unified 3D coordinate system to determine the user's perspective view of the AR display 300. The Interaction Engine generates a rendering of the 3D virtual medical model 304 in the virtual container 302 according to the model pose data for display to the user in the AR display 300 according to the user's perspective view.

Various embodiments described herein provide functionality for selection of virtual objects based on directional data associated with the 3D virtual hands, detection of physical body parts (such as a user's hand(s)) or a position and orientation of a physical instrument (i.e. physical instrument pose). For example, the Interaction Engine tracks the user's hands and/or the physical instrument via one or more tracking algorithms to determine hand direction(s) or instrument directions to further be utilized in determining whether one or more hand gestures and/or instrument gestures performed by the user indicate selection of a virtual object and/or one or more types of functionalities accessible via the AR display 300. For example, the Interaction Engine may track the user's hands and determine respective positions and changing positions of one or more hand joints. For example, the Interaction Engine may track the tip of a physical instrument, a virtual extension of the physical instrument and/or a virtual offset of the physical instrument and determine respective positions and changing positions of one or more portions of the physical instrument. In various embodiments, the Interaction Engine may implement a simultaneous localization and mapping (SLAM) algorithm.

The Interaction Engine may generate directional data based at least in part on average distances between the user's palm and the user's fingers and/or hand joints or distances between portions (physical portions and/or virtual portions) of a physical instrument. In some embodiments, the Interaction Engine generates directional data based on detected directional movement of the AR headset device worn by the user. The Interaction Engine determines that the directional data is based on a position and orientation of the user's hand(s) (or the physical instrument) that indicates a portion(s) of a 3D virtual object with which the user seeks to select and/or virtually interact with and/or manipulate.

Figure 3D:
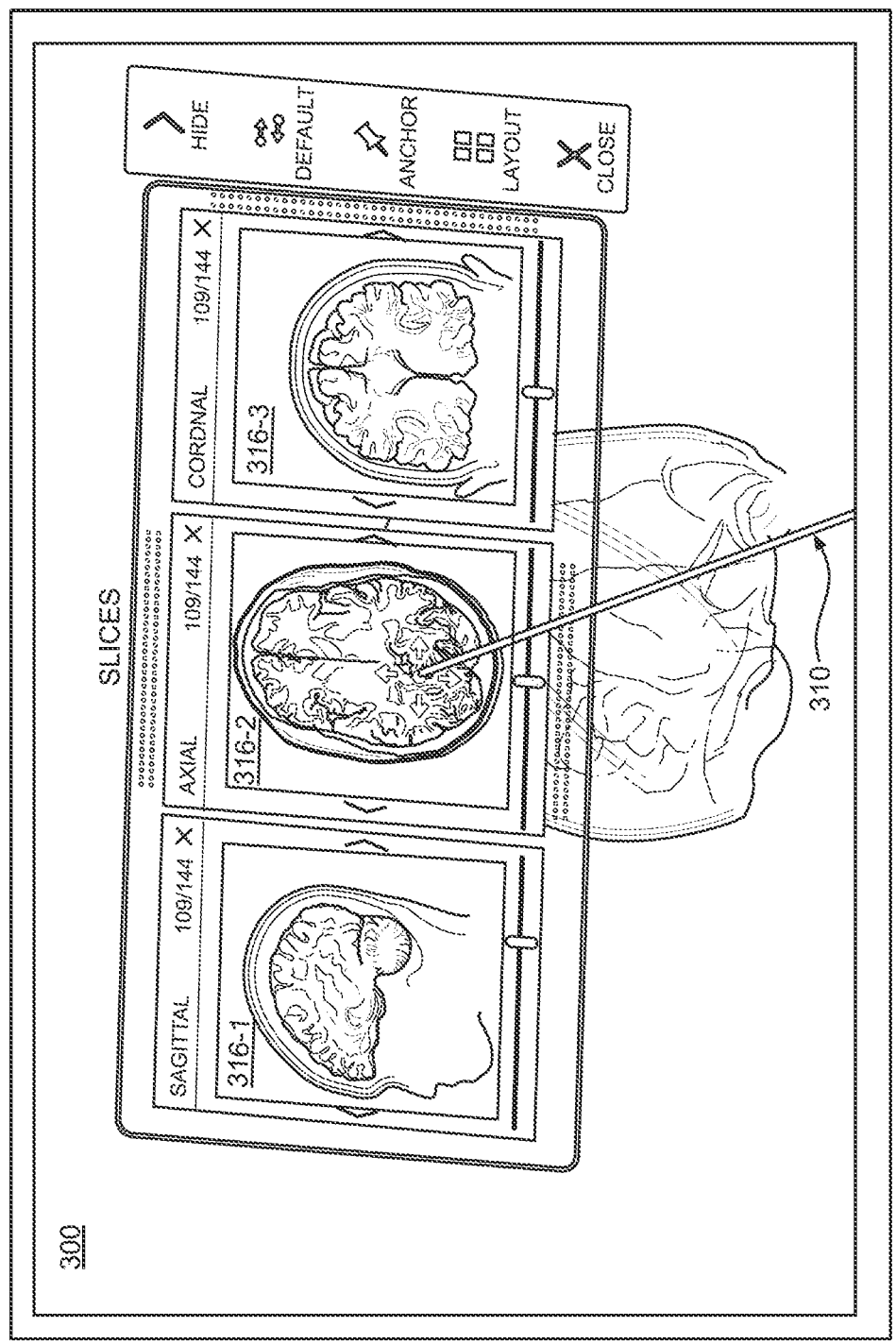

In some embodiments, as shown in FIG. 3D, the Interaction Engine may implement a ray casting algorithm to generate a selection ray 310 displayed in the AR display 300 extending from the user's hands or physical instrument to a virtual object. For example, the terminal portion 310-1 of the selection ray 310 may have the same positional coordinates as a displayed portion of a virtual object. The displayed portion having the same positional coordinates may be identified by the Interaction Engine as a portion of the virtual object the user seeks to select and/or virtually interact with or manipulate.

According to various embodiments, the Interaction Engine may implement a collision algorithm to determine a portion of a virtual object the user seeks to select and/or virtually interact with. For example, the Interaction Engine may track the user's hands and/or the physical instrument according to respective positional coordinates in the unified 3D coordinate system that correspond to the orientation of the user's hands and/or the physical instrument in the physical world. The Interaction Engine may detect that one or more tracked positional coordinates may overlap (or be the same as) one or more positional coordinates for displaying a particular portion(s) of a virtual object. In response to detecting the overlap, the Interaction Engine may determine that the user seeks to select and/or virtually interact with the portion(s) of the particular virtual object displayed at the overlapping positional coordinates.

According to various embodiments, upon determining the user seeks to select and/or virtually interact with a virtual object, the Interaction Engine may detect one or more changes in hand joint positions and/or physical instrument positions and identify the occurrence of the position changes as a performed selection function. For example, a performed selection function may represent an input command to the Interaction Engine confirming the user is selecting a portion of a virtual object via the ray casting algorithm and/or collision algorithm. For example, the performed selection function may also represent an input command to the Interaction Engine confirming the user is selecting a particular type of virtual interaction functionality. For example, the user may perform a physical gesture of tips of two fingers touching to correspond to a virtual interaction representing an input command, such as a select input command.

As shown in FIG. 3A, a slice panel selection virtual interaction includes activation of a 3D virtual menu 312 in response to detecting a physical gesture defined as an input command for requesting display of the 3D virtual menu 312. For example, such a physical gesture may be defined as detecting a user presenting a hand to a camera view of the AR headset device for a particular amount of time. Upon detection that the particular amount of time has lapsed, the Interaction Engine displays the 3D virtual menu 312 in the AR display 300. For example, the Interaction Engine determines a first display position, in the unified 3D coordinate space, of the 3D virtual menu 312 based on positional coordinates associated with the detected physical gestures. The Interaction Engine displays the 3D virtual menu 312 in the AR display 300 at the first display position.

As shown in FIG. 3B, the Interaction Engine detects a subsequent physical gesture with respect to the 3D virtual menu 312. For example, the Interaction Engine may track positional coordinates of the user's finger to determine the user is selecting a slice functionality 312-1 from the 3D virtual menu 312.

As shown in FIG. 3C, upon receipt of the user selection, the Interaction Engine determines a second display position and orientation, in the unified 3D coordinate space, for a 3D virtual slice panel 316 and displays the 3D virtual slice panel 316 at the second display position and orientation. The 3D virtual slice panel 316 may include a plurality of slices 316-1, 316-2, 316-3. For example, the 3D virtual slice panel 316 may include a virtual sagittal slice 316-1 of a particular slice layer, a virtual axial slice 316-2 of another slice layer and a virtual coronal slice 316-3 of yet another different slice layer. It is understood that the respective slice layers portrayed in the slices 316-1, 316-2, 316-3 represent various portions of 3D medical model data and may further represent various differing portions of 3D medical model data.

As shown in FIG. 3D, various embodiments of the Interaction Engine provide for manipulation of the slice panel 316 by a selection of the slice panel 316 via a selection ray 310. In various embodiments, selection of the slice panel 316 can also be activated via a collision algorithm, e.g. the Interaction Engine detects that the position and orientation of the user's hand(s) collides (i.e. overlaps) with the position and orientation of the virtual slice panel 316.

Figure 3E:
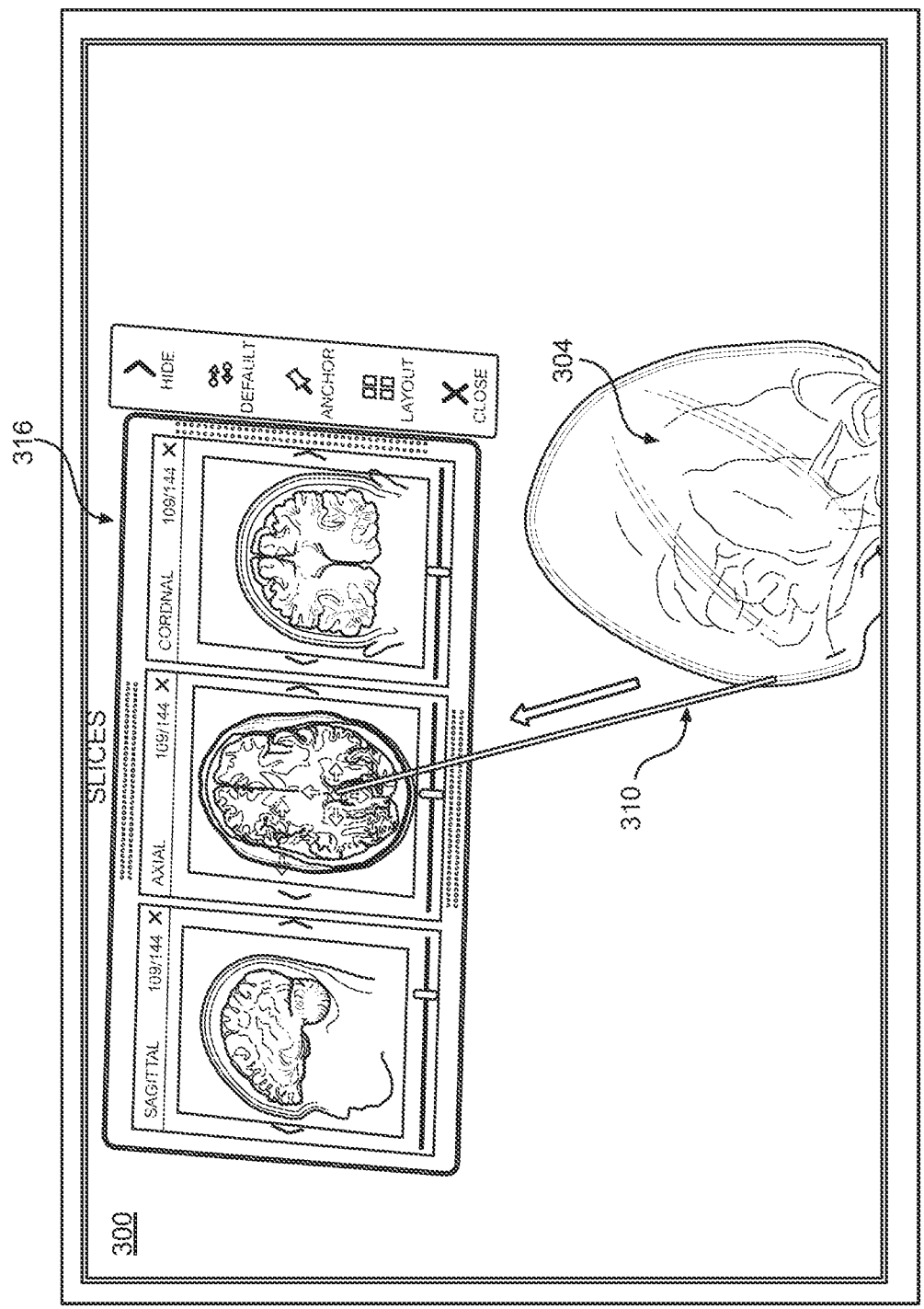

As shown in FIG. 3E, upon detecting selection of the slice panel 316, the Interaction Engine tracks positional coordinates with respect to movement of the user's hand associated with the selection ray 310. The Interaction Engine updates a display position of the slice panel 316 resulting from movement of the selection ray 310. The Interaction Engine determines the positional coordinates a display positions for movement of the selection ray 310 based on the tracked movement of the user's hands. For example, Interaction Engine may detect forward movement of the user's hand thereby updating a display position for the slice panel 316 that portrays the slice panel 316 as farther away, according to a linear perspective view, with respect to the AR headset device's current device pose data. During manipulation of slice panel 316, the orientation of the slice panel 316 is always facing towards the user such that the slices displayed in the slice panel 316 are in visible to the user.

Figure 3F:
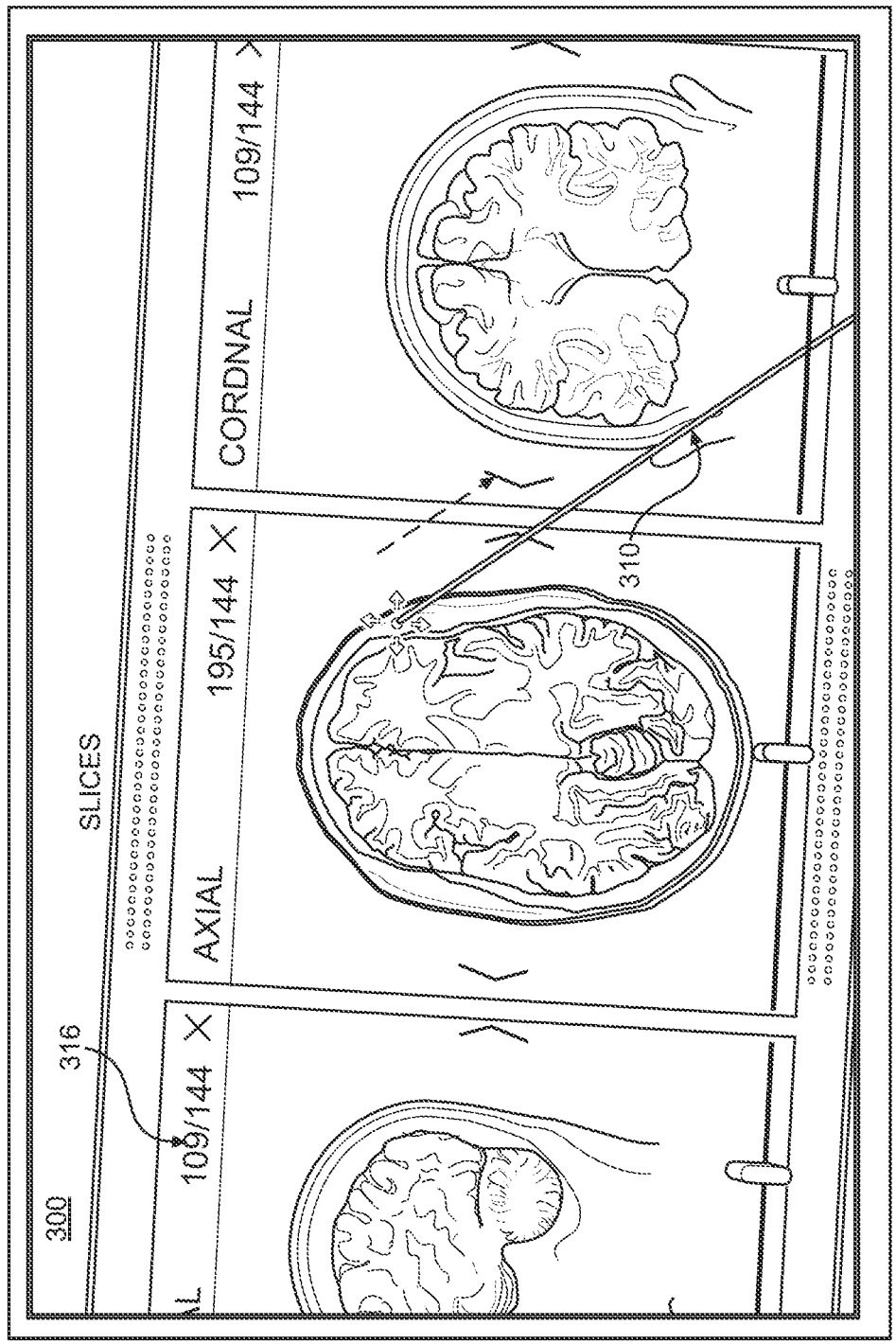

As shown in FIG. 3F, the Interaction Engine detects backward movement of the user's hand thereby updating a display position for the slice panel 316 that portrays the slice panel 316 as closer according to the linear perspective view.

Figure 4:
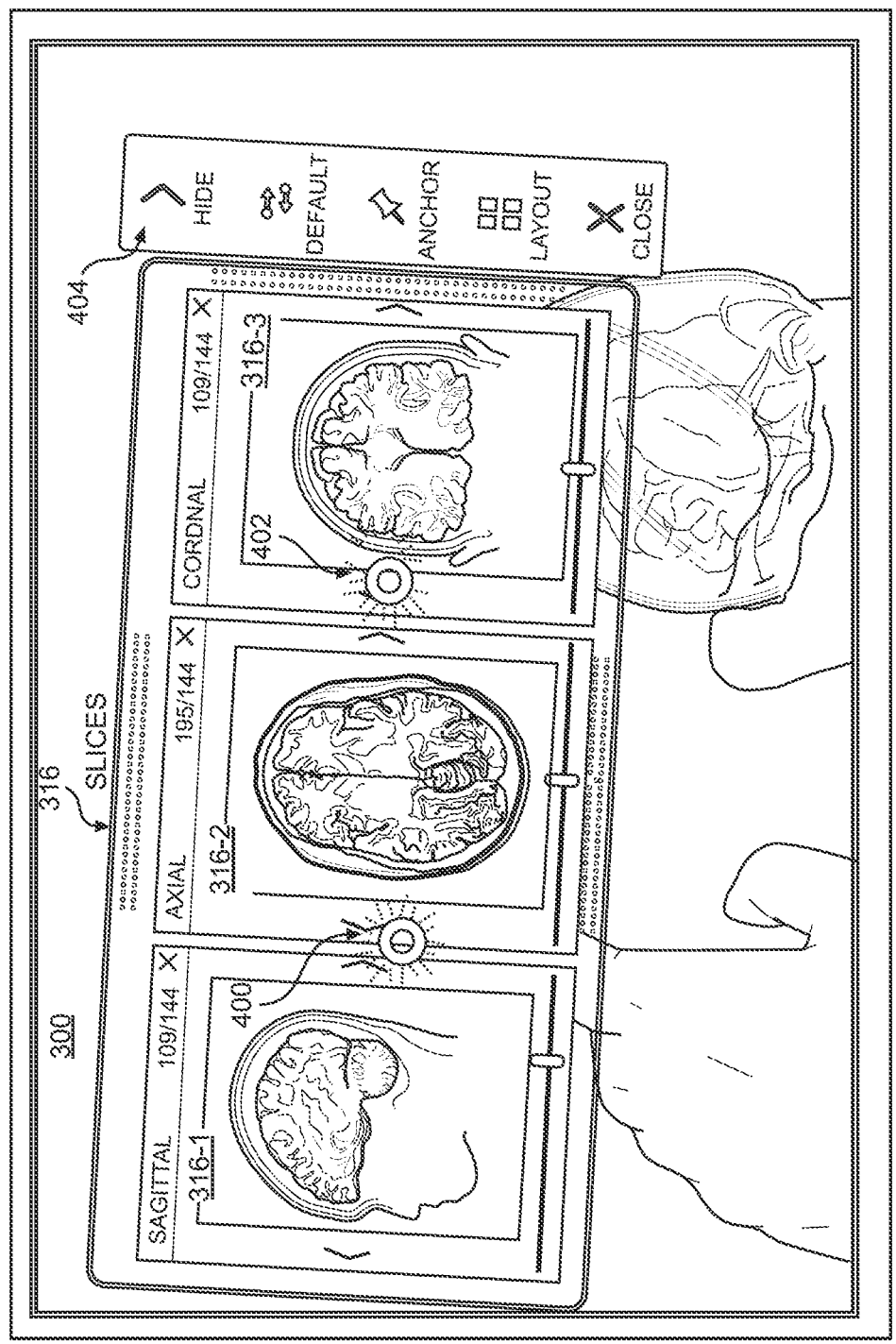
FIG. 4 is a diagram illustrating an exemplary environment in which some embodiments may operate.

One or more embodiments of the Interaction Engine may implement a slice layer scroll virtual interaction. As shown in FIG. 4, the slice layer scroll virtual interaction may be a selection of a slice scroll buttons 400, 402. Selection of a slice scroll button 400, 402 may increment and/or decrement a current slice layer currently portrayed in a corresponding slice view 316-1, 316-3. For example, upon detecting selection of a slice scroll button 400 for the sagittal slice 316-1, the Interaction Engine updates the current slice layer 109 of sagittal slice 316-1 to display medical model data from the updated slice layer. It is understood that slice scroll buttons 400, 402 provide for functionality similar to the 2D slice buttons 204-1, 204-2. In addition, the slice panel 316 is further displayed in the AR display 300 with a slice panel menu 404. The slice panel manipulation virtual interaction includes one or more functionalities such as: enlargement, zoom-in and zoom-out in response to detection by the Interaction Engine of a physical gesture(s).

Figure 5A:
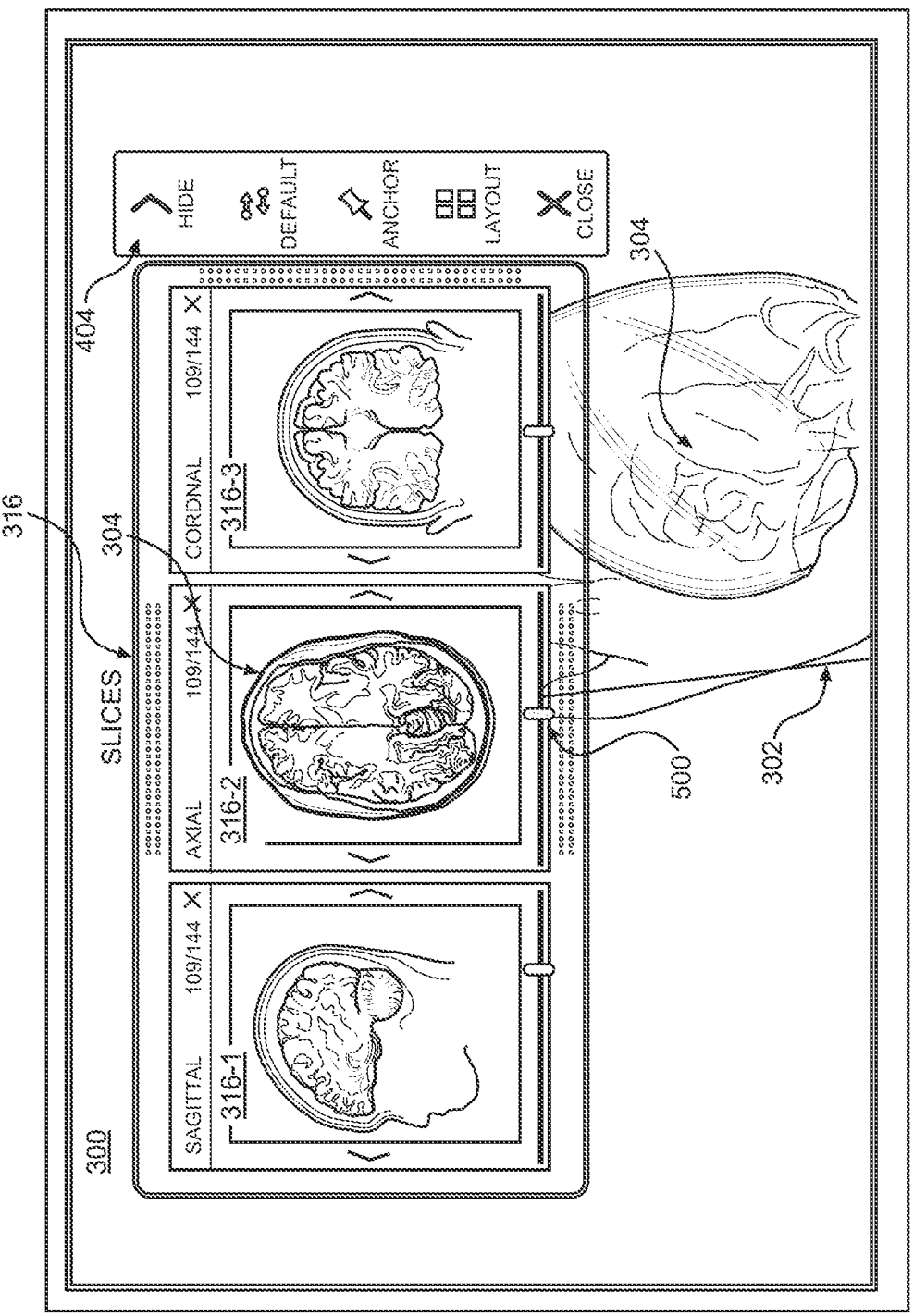
FIGS. 5A and 5B are each a diagram illustrating an exemplary environment in which some embodiments may operate.
Figure 5B:
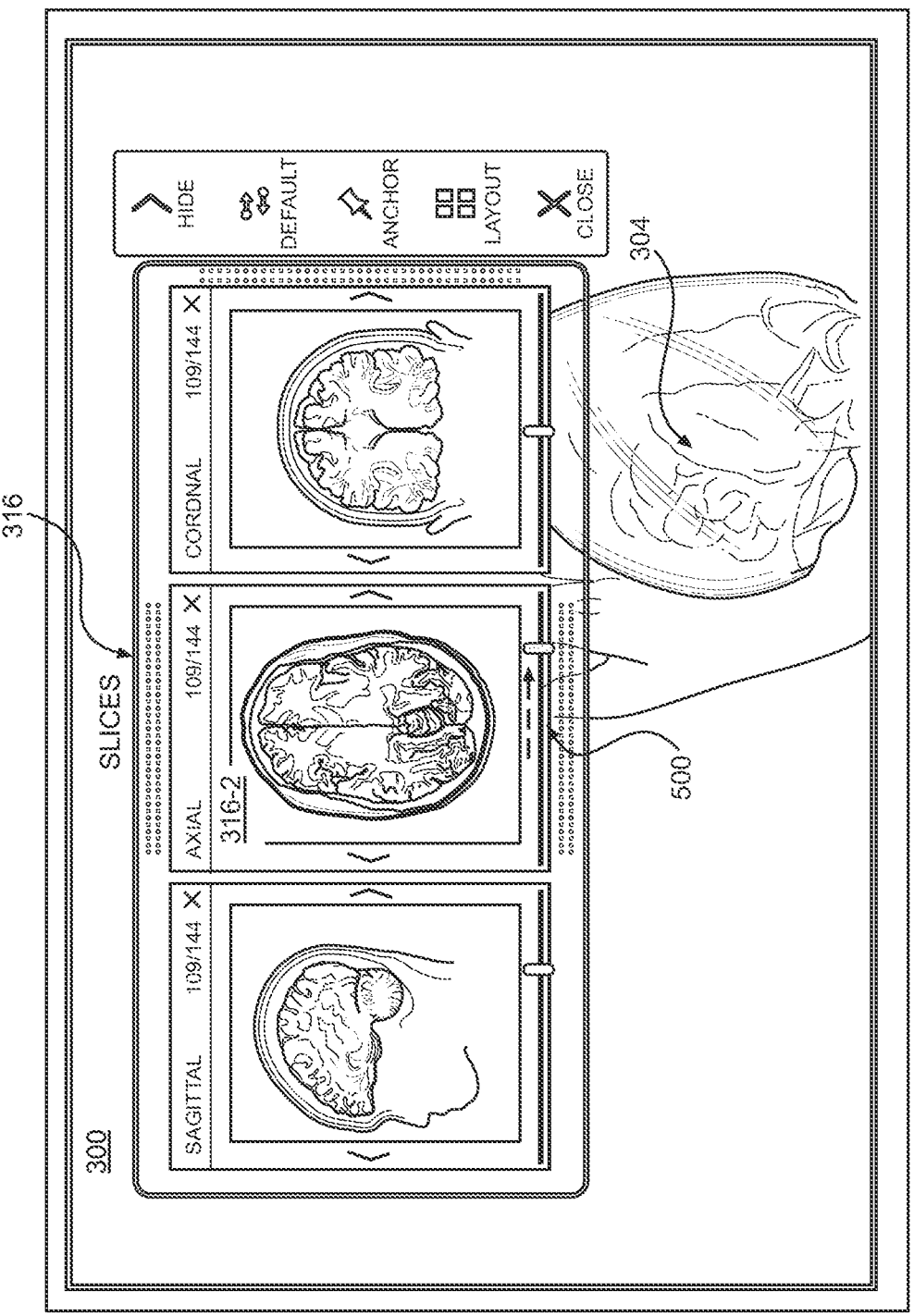

As shown in FIG. 5A, a slice layer scroll virtual interaction may be a selection of a slice panel scroll-bar 500. The Interaction Engine may detect selection of the scroll-bar 500. As shown in FIG. 5B, upon detecting one or more subsequent detected physical gestures, the Interaction Engine determines directional data from the subsequent physical gestures to be applied to the selected scroll-bar 500. For example, such subsequent detected physical gesture may correspond to directional data indicating a requested movement of the scroll-bar 500 towards the right or towards the left.

The Interaction Engine modifies the AR display 300 to present an animation of the scroll-bar 500 moving according to the directional data. As the Interaction Engine portrays the scroll-bar 500 moving according to the directional data, the Interaction Engine updates the corresponding slice 316-2 in the slice panel 316 according to the respective position of the scroll-bar 500.

For example, subsequent detected movements may correspond to one or more virtual interactions for selection and movement of the scroll-bar 500 such that the Interaction Engine updates a display position of the scroll-bar 500. The updated display position of the scroll-bar 500 thereby corresponds to a different slice layer of the medical model data. The Interaction Engine identifies medical model data for the different slice layer and generates a 2D graphic representation of the identified medical model data that corresponds to the different slice layer. The Interaction Engine updates display of the slice 316-2 with a rendering of the identified medical model data.

Figure 6A:
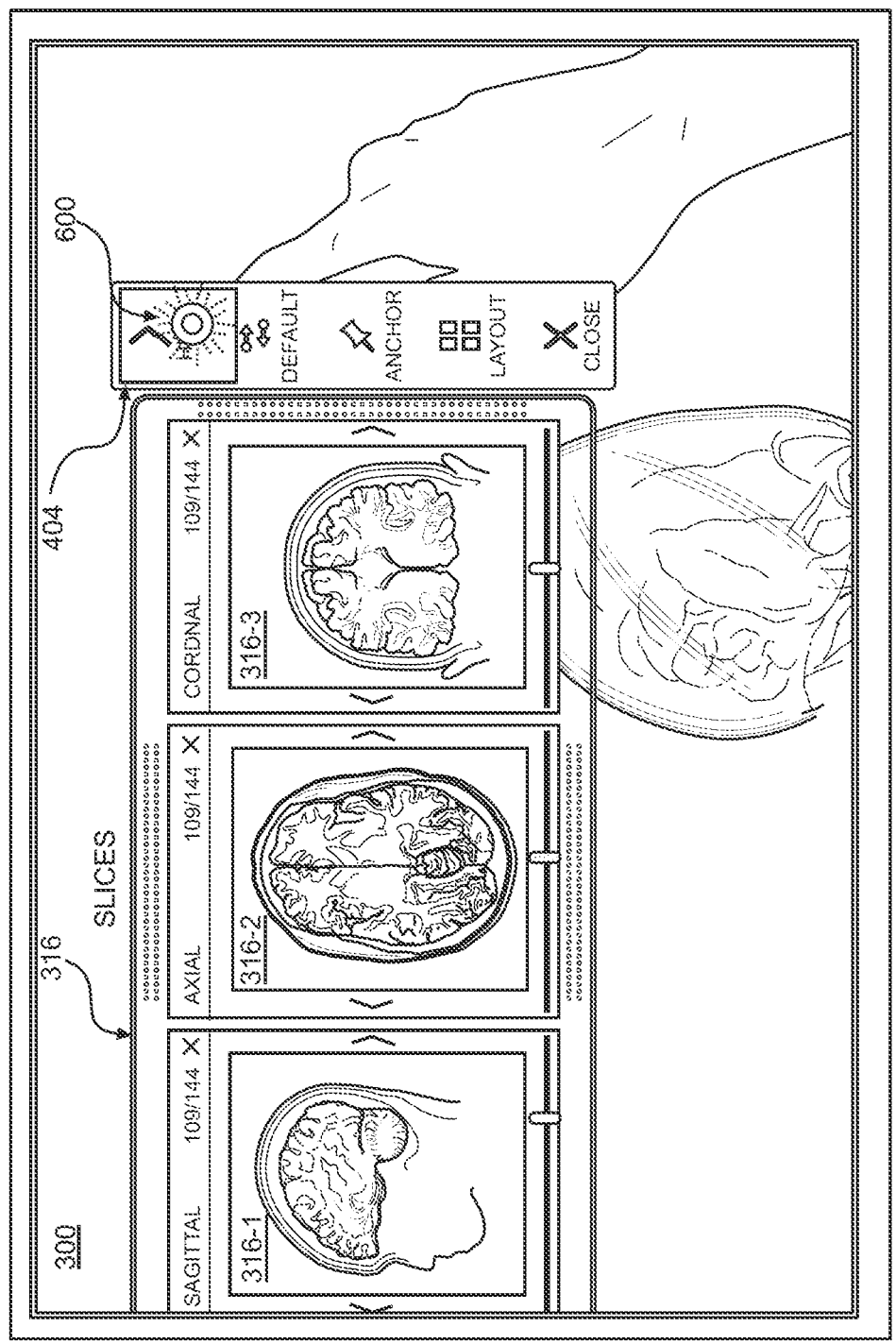
FIGS. 6A and 6B are each a diagram illustrating an exemplary environment in which some embodiments may operate.
Figure 6B:
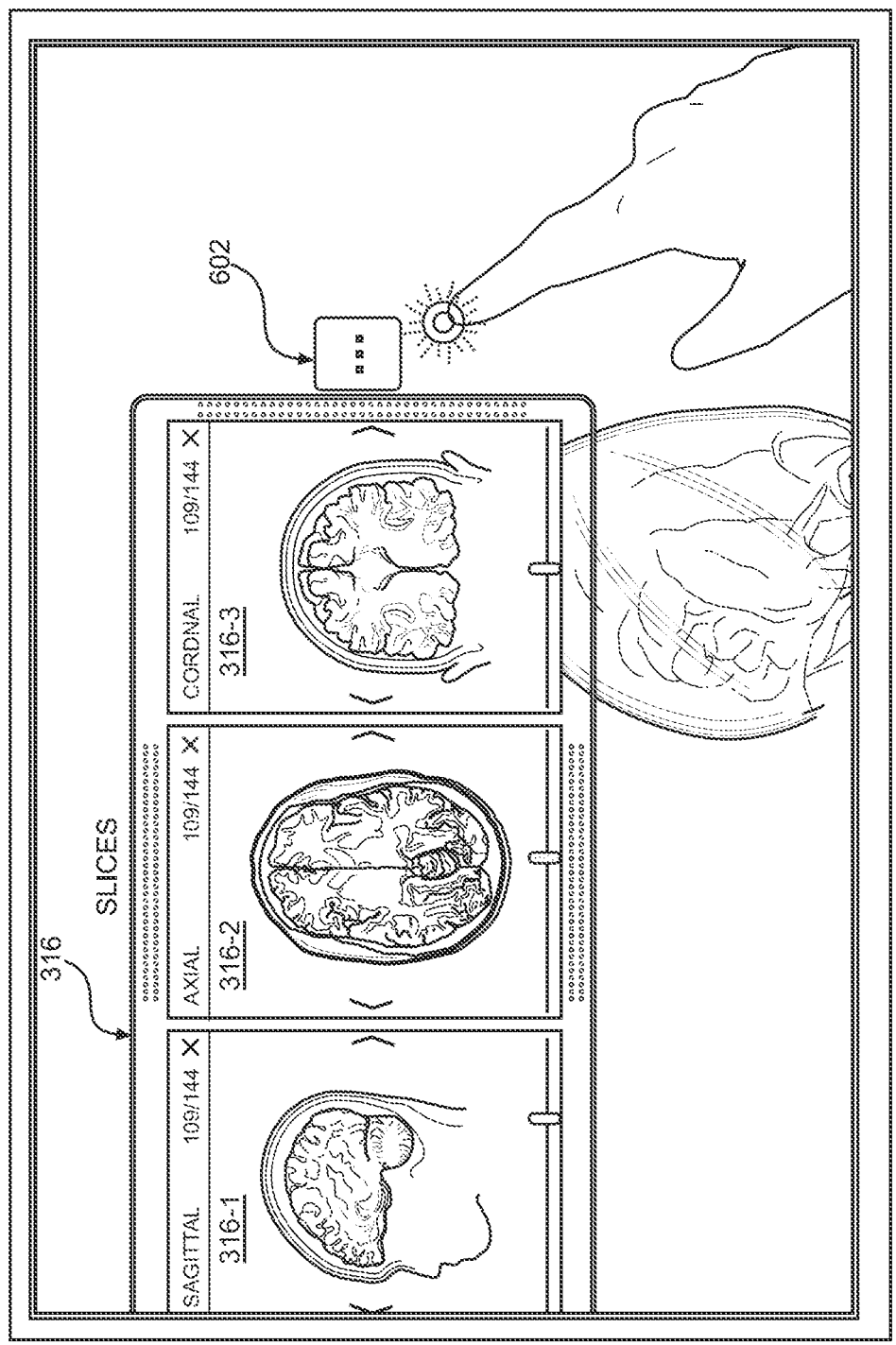

Various embodiments of the Interaction Engine may implement a slice panel control virtual interaction. As shown in FIG. 6A, the slice panel control virtual interaction includes selection of a slice panel menu hide button 600. According to various embodiments, the Interaction Engine detects selection of the hide button 600 from the slice panel menu 404. As shown in FIG. 6B, upon detection of the selection of the hide button 600, the Interaction Engine replaces display of the slice panel menu 404 with a collapsed menu 602. It is understood that selection of the collapsed menu 602 results in the Interaction Engine replacing display of the collapsed menu 602 with display of the slice panel menu 404.

Figure 7A:
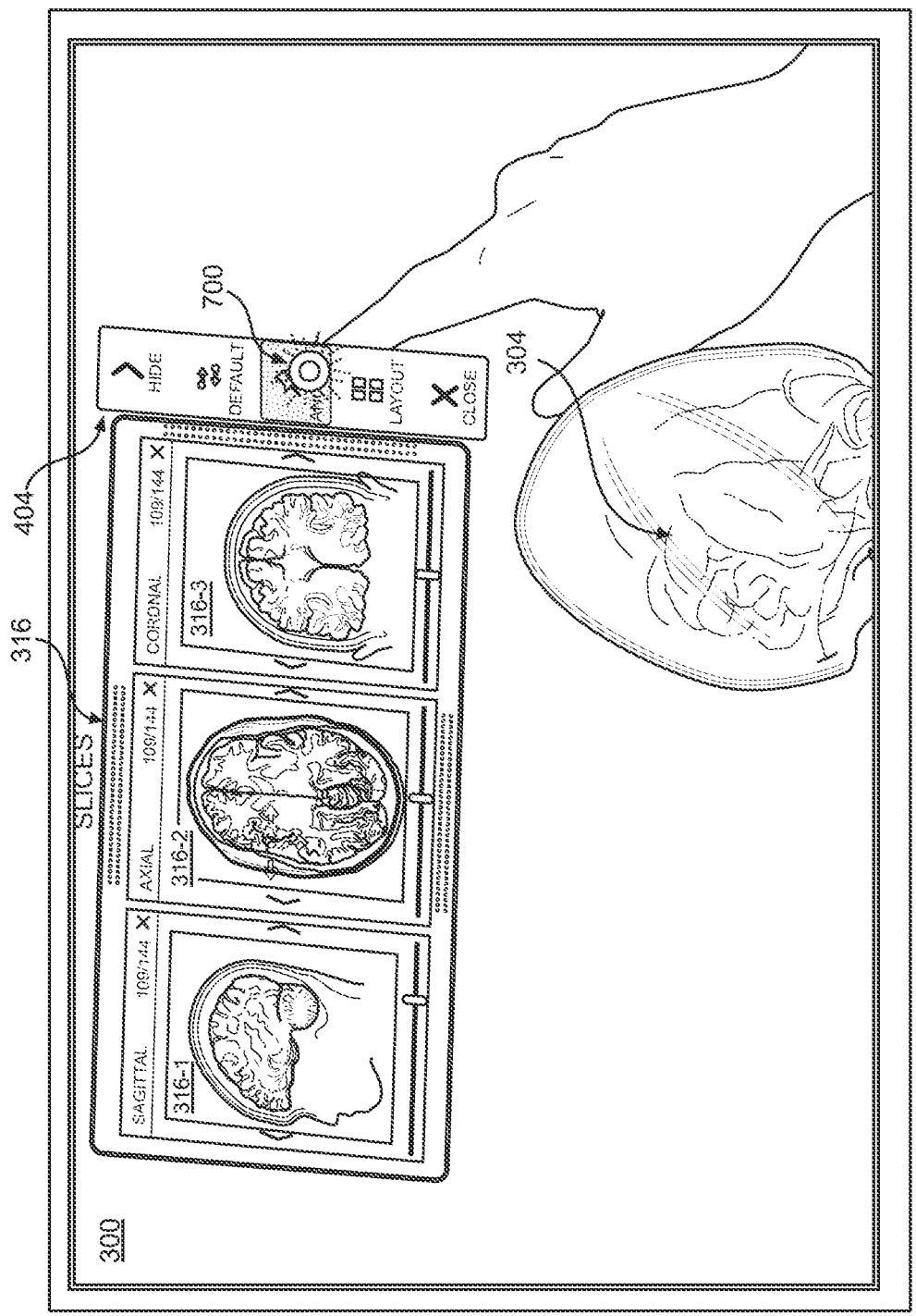
FIGS. 7A and 7B are each a diagram illustrating an exemplary environment in which some embodiments may operate.

As shown in FIG. 7A, the slice panel control virtual interaction includes selection of a slice panel anchor button 700. The Interaction Engine detects selection of the anchor button 700 from the 3D virtual slice panel menu 404 while the menu 404 is adjacently displayed with respect to a current display position of the 3D virtual slice panel 316. When selection of the anchor button 700 is detected, the Interaction Engine disables (or deactivates) subsequent manipulation of and on the slice panel 316. When the Interaction Engine detects de-selection of the anchor button 700, the Interaction Engine enables (or activates) subsequent manipulations s of an on the slice panel 316.

Figure 7B:
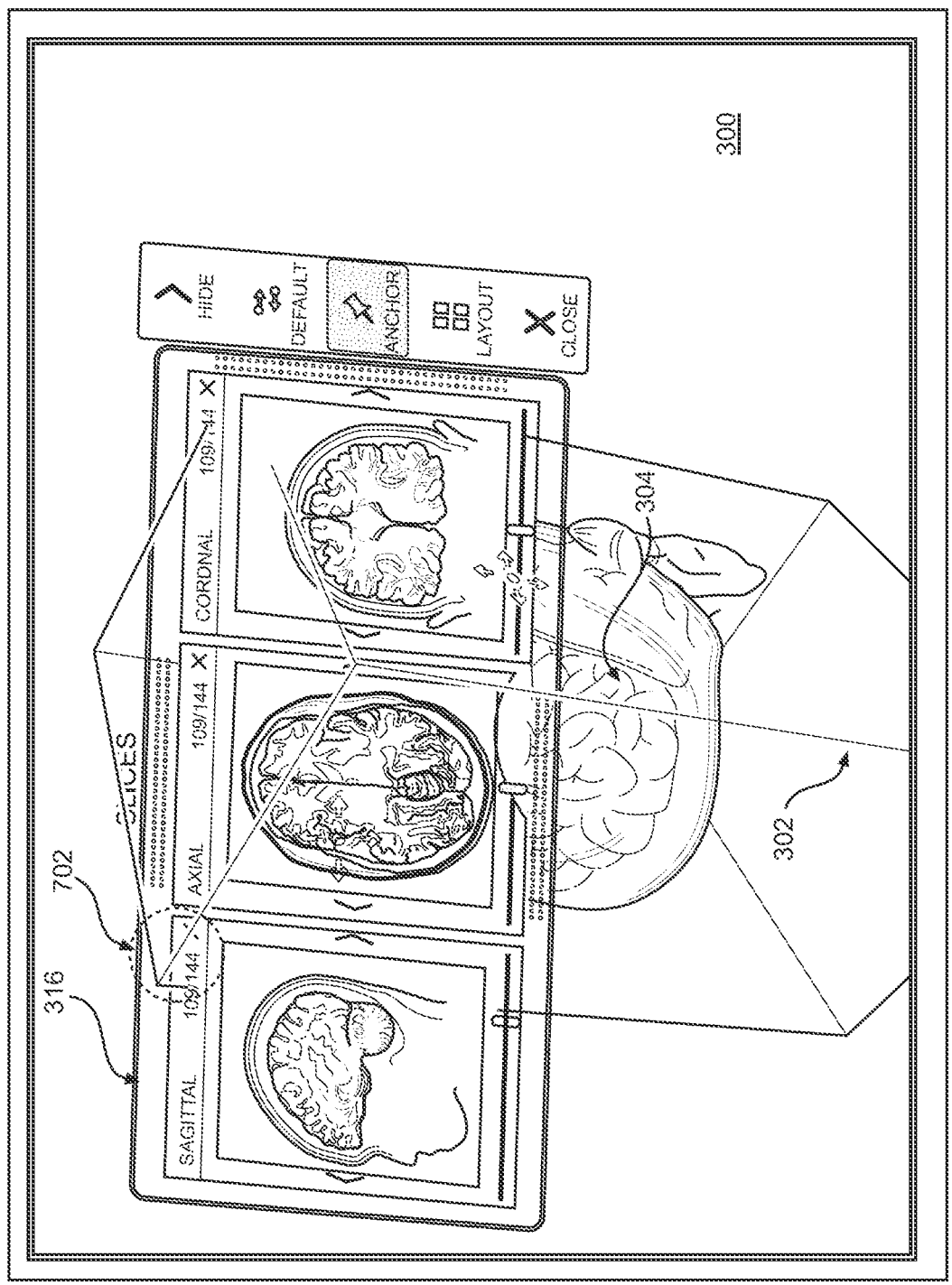

As shown in FIG. 7B, the Interaction Engine maintains display of a state of the 3D virtual slice panel 316 present at the moment of selection of the anchor button 700. For example, the state of the slice panel 316 may be the particular slice layers portrayed by each of the views 316-1, 316-2, 316-3 when anchor button 700 is selected. The Interaction Engine detects and tracks a subsequent physical gesture(s) with respect to a 3D virtual object(s), such as the virtual container 302 and the virtual medical model 304, that is concurrently displayed with the slice panel 316. For example, the detected subsequent physical gesture(s) may result in movement of the virtual container 302 from a current display position to respective updated display positions.

During movement of the virtual container 302, the Interaction Engine determines an intersection 702 between the anchored slice panel 316 and a current display position of the virtual container 302. For example, the Interaction Engine identifies positional container coordinates within the interior of the virtual container 302 that are included in parts of the slice panel 316.

Due to the selected anchor button 700, the Interaction Engine maintains the state of the slice panel 316 such that any detected physical gestures with respect to the virtual container 302 will not result in any modification of the display and/or display position of the slice panel 316 and will not result in any selection (or user manipulation) directed at the virtual container 302 being misapplied to the slice panel 316.

Figure 8A:
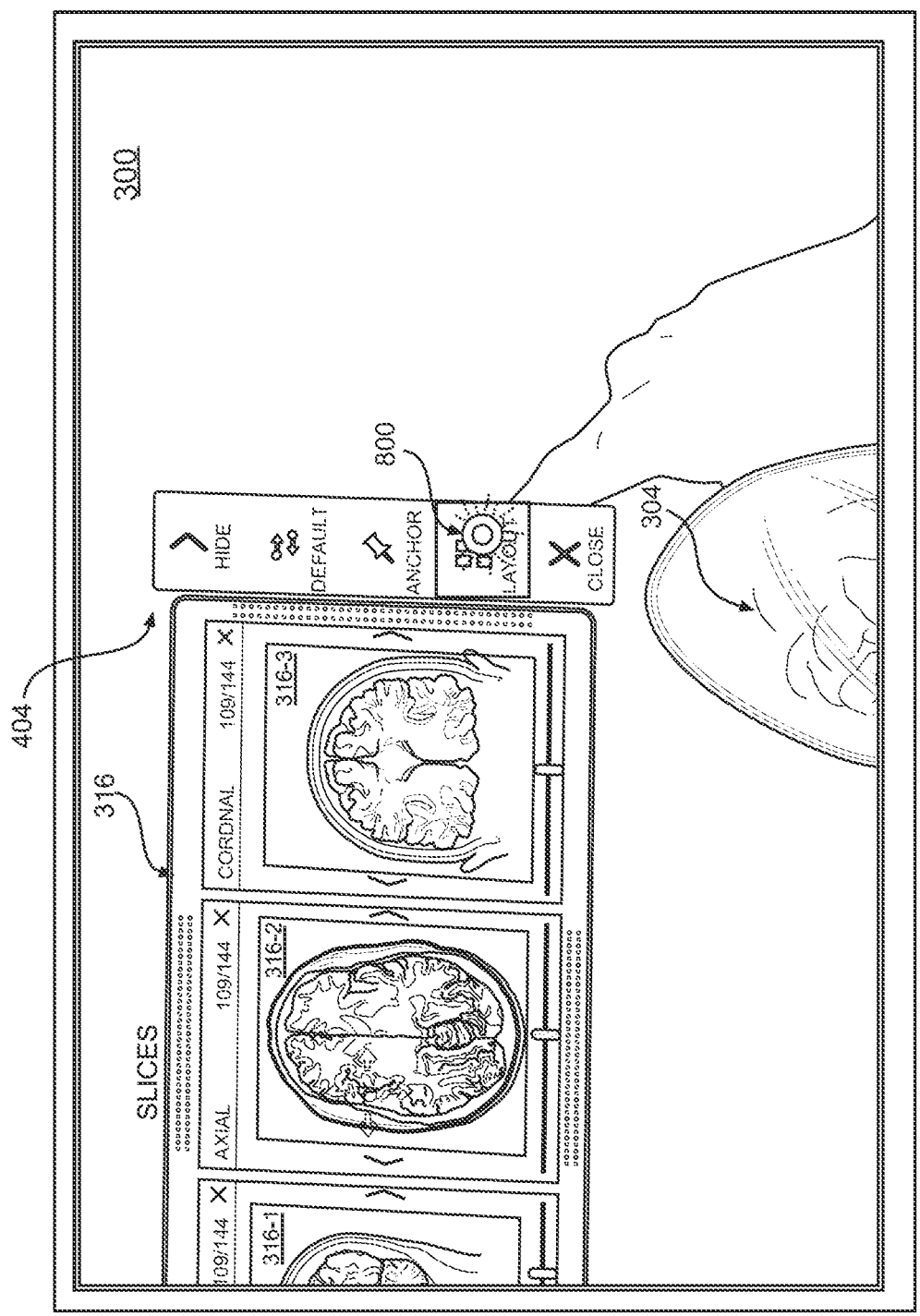
Figure 8C:
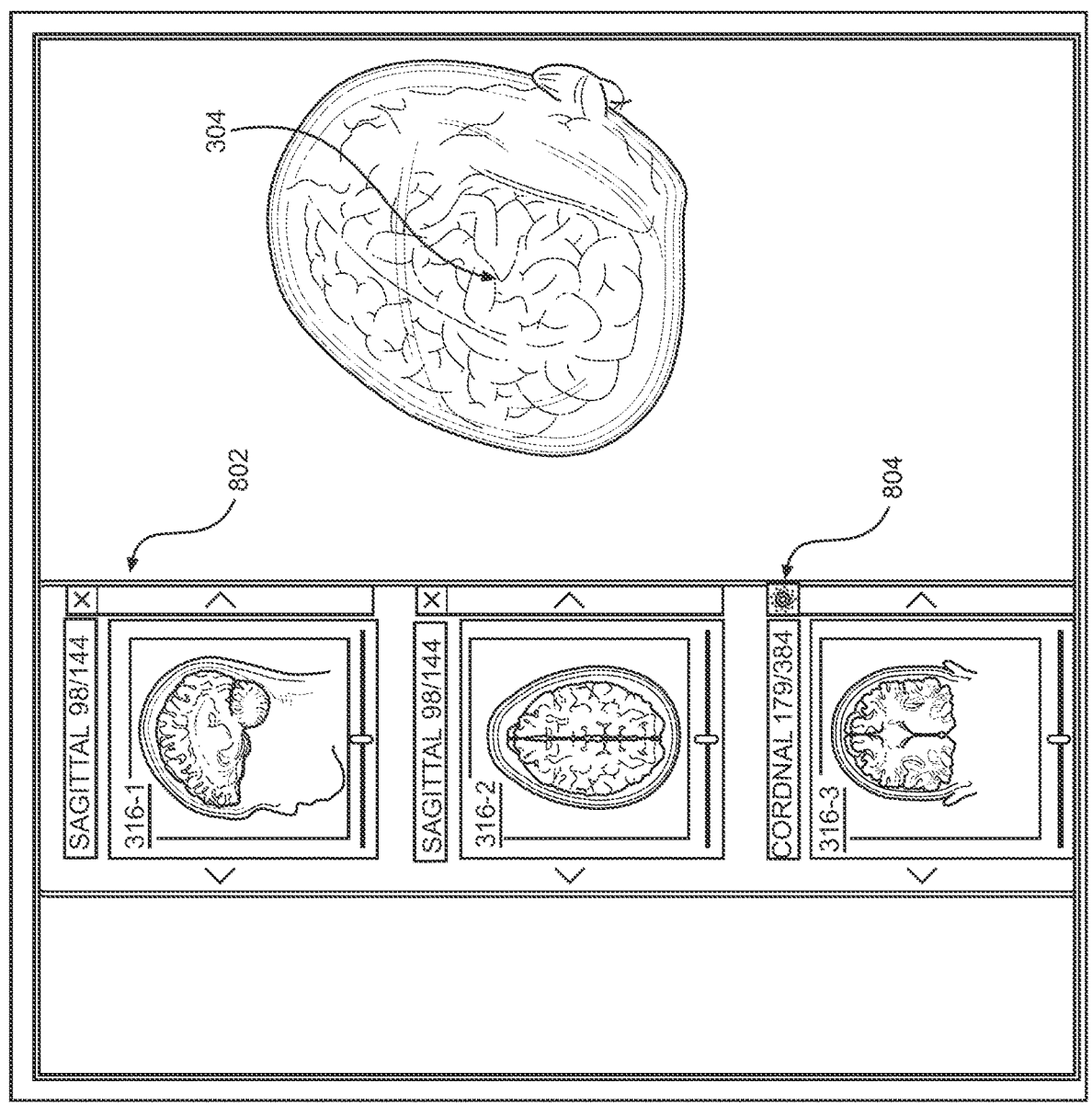

As shown in FIG. 8A, the slice panel control virtual interaction includes selection of a slice panel layout button 800. As shown in FIG. 8B, the Interaction Engine modifies the AR display 300 with an updated 3D virtual slice panel 802 displayed according to a vertical layout. As shown in FIG. 8C, the slice panel control virtual interaction may also include selection of a slice close button 804. As shown in FIG. 8D, in response to detecting selection of the slice close button 804 associated with the coronal view 316-3, the Interaction Engine further modifies the AR display 300 to include an updated 3D virtual slice panel 806 that includes display of only the sagittal and axial slices 316-1, 316-2. It is understood that each of the slices 316-1, 316-2, 316-3 may have a corresponding slice close button.

Figure 9A:
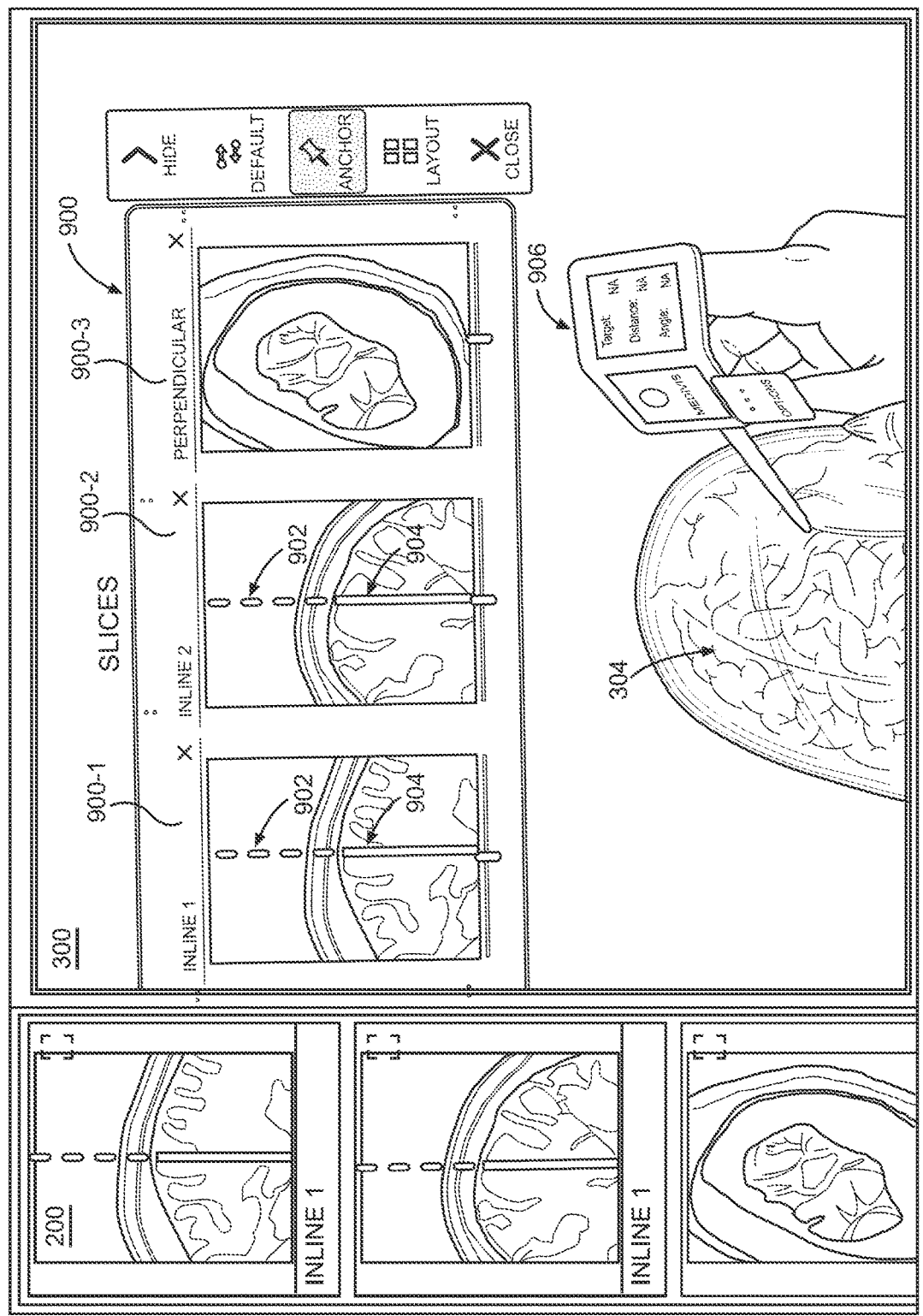
FIGS. 9A, 9B, 9C, 9D, 9E, 9F and 9G are each a diagram illustrating an exemplary environment in which some embodiments may operate.

As shown in FIG. 9A, an embodiment(s) of the Interaction Engine may implement an inline slice panel 900 while the inline mode is active. The inline slice panel 900 includes respective slices 900-1, 900-2, 900-3 in place of the sagittal, axial and coronal slices 316-1, 316-2, 316-3 of the slice panel 316. The first and second inline slices 900-1, 900-2 include display of an instrument indicator that includes a first portion 902 that represents the body of the instrument 906 according to the current position and orientation of the physical instrument 906 (i.e. instrument pose data). The instrument indicator further includes a second portion 904 that represents an extension of the instrument 906 according to the physical instrument's 906 current position and orientation. The first portion 902 and the second portion 904 are visually distinct from each other. In one or more embodiments, the Interaction Engine updates the 2D display 200 with 2D representations of the inline views 900-1, 900-2, 900-3.

Figure 9B:
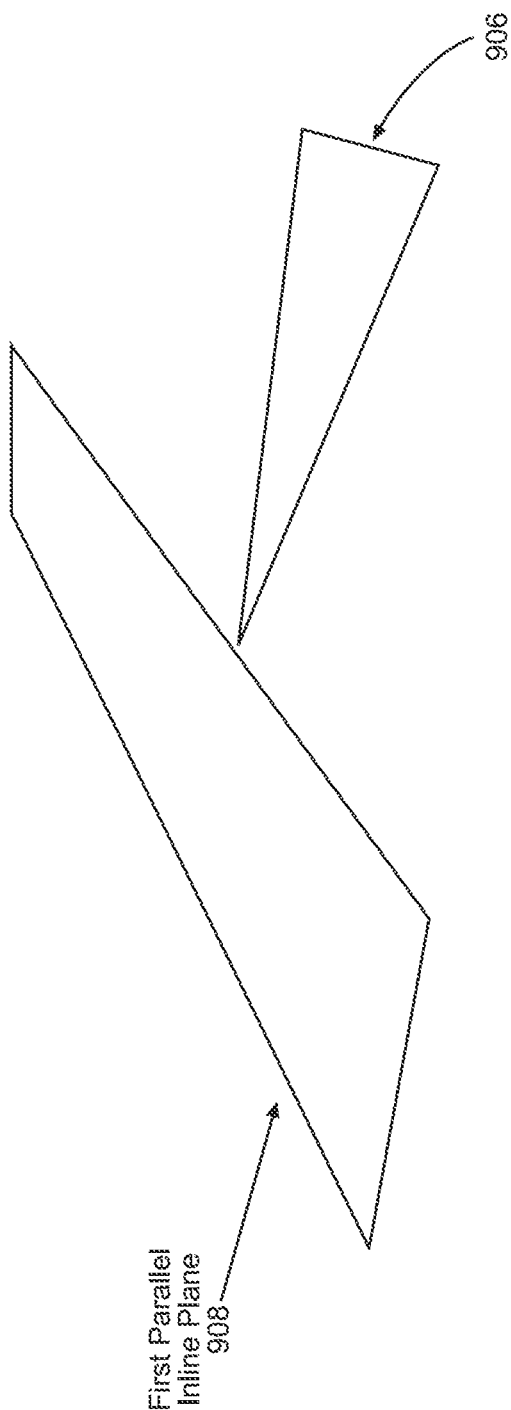

As shown in FIG. 9B, the first inline slice 900-1 of the inline slice panel 900 is based on a first parallel inline plane 908. The first parallel inline plane 908 runs parallel to the current position and orientation of the instrument 906. The first slice 900-1 thereby represents a slice layer comprised of respective medical model data of the medical model 302, displayed according to a current model pose, that maps to positional coordinates that lie on the first parallel inline plane 908.

Figure 9C:
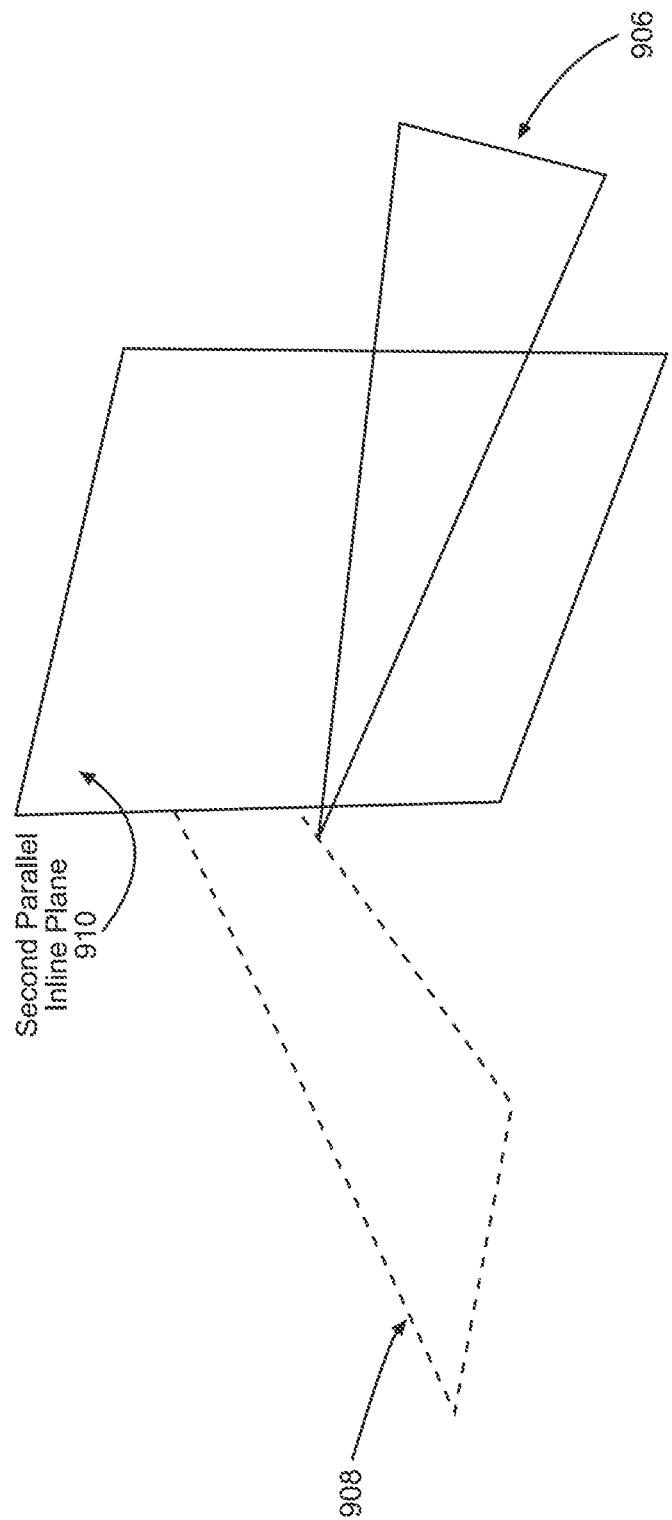

As shown in FIG. 9C, the second inline slice 900-2 of the inline slice panel 900 is based on a second parallel inline plane 910. The second parallel inline plane 910 runs parallel to the physical instrument 906 according to the current position and orientation of the instrument 906. The second parallel inline plane 910 is also perpendicular to the first parallel inline plane 908. The second view 900-2 represents a slice layer comprised of respective medical model data of the medical model 302, displayed according to the current model pose, that maps to positional coordinates that lie on second parallel inline plane 910.

Figure 9D:
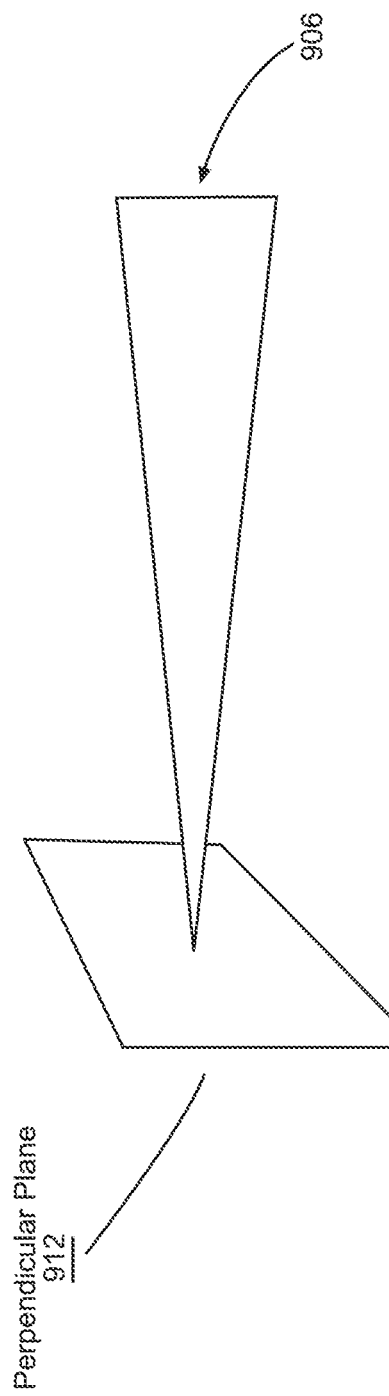

As shown in FIG. 9D, the third inline slice 900-3 of the inline slice panel 900 represents a slice layer comprised of respective medical model data of the medical model 302, displayed according to a current model pose, that maps to positional coordinates that lie on a plane 912 that is perpendicular to a current orientation and position of a portion of the physical instrument 906. The third inline slice is also referred as perpendicular slice.

Figure 9E:
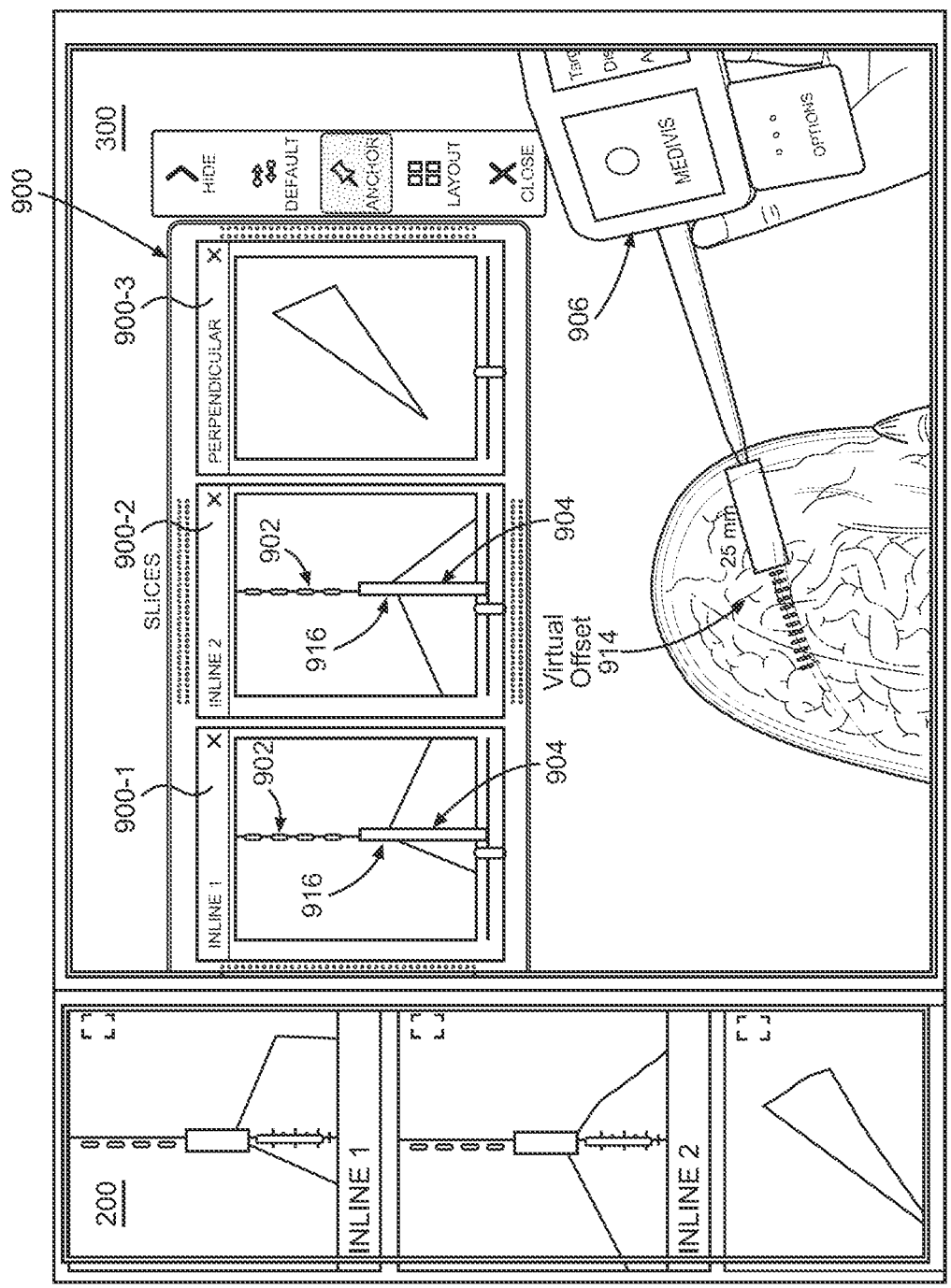

As shown in FIG. 9E, an embodiment(s) of the Interaction Engine may implement an inline slice instrument virtual interaction while the inline mode is active. The inline view instrument virtual interaction further includes a representation 916 of a virtual offset 914 of the physical instrument 906 in the instrument indicator displayed in the first and second inline slices 900-1, 900-2. Similar to the first and second portions 902, 904 of the instrument indicator, the representation 916 of a virtual offset 914 is displayed according to the current position and orientation of the physical instrument 906 and its virtual offset 914.

Figure 9F:
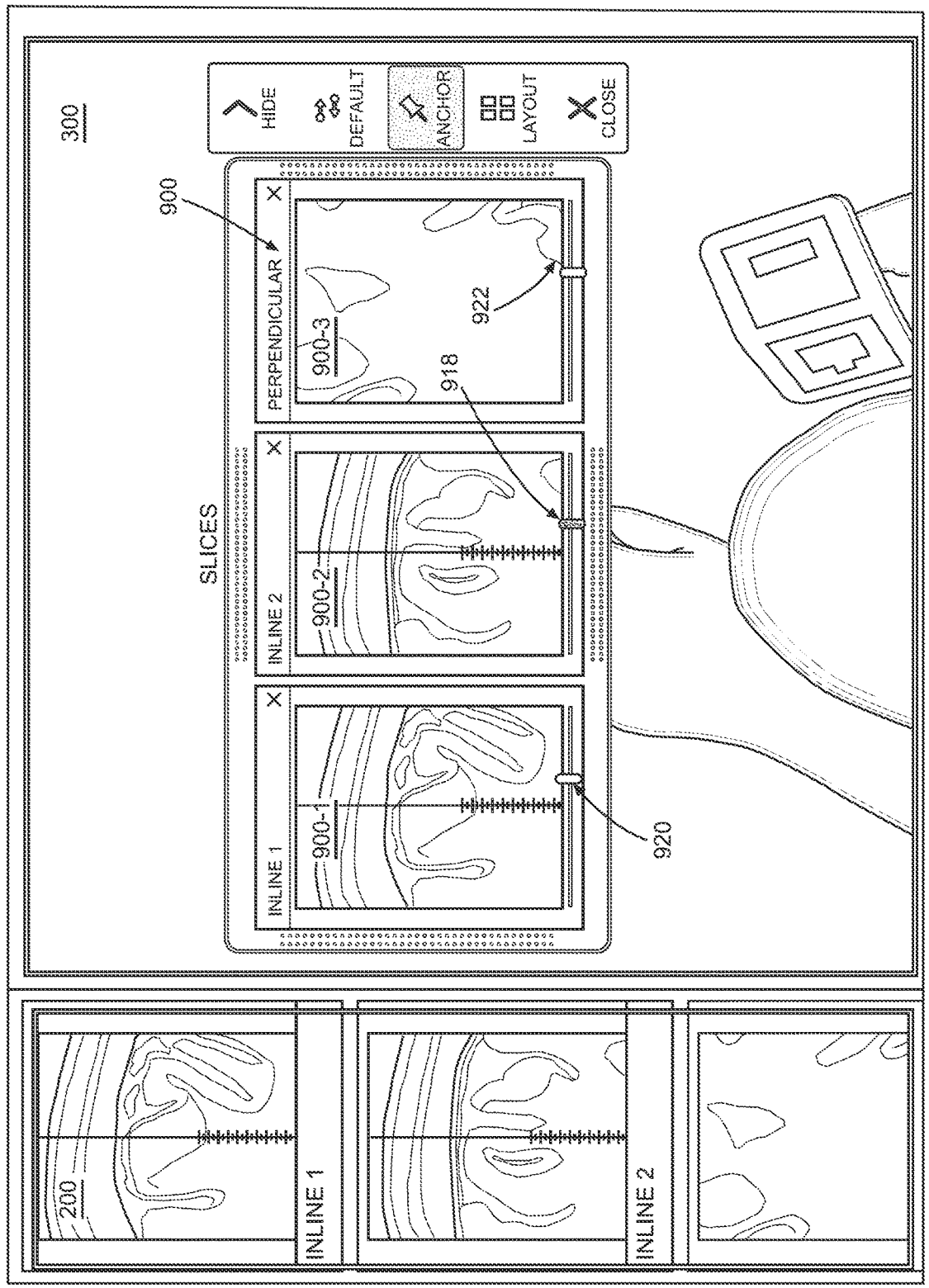
Figure 9G:
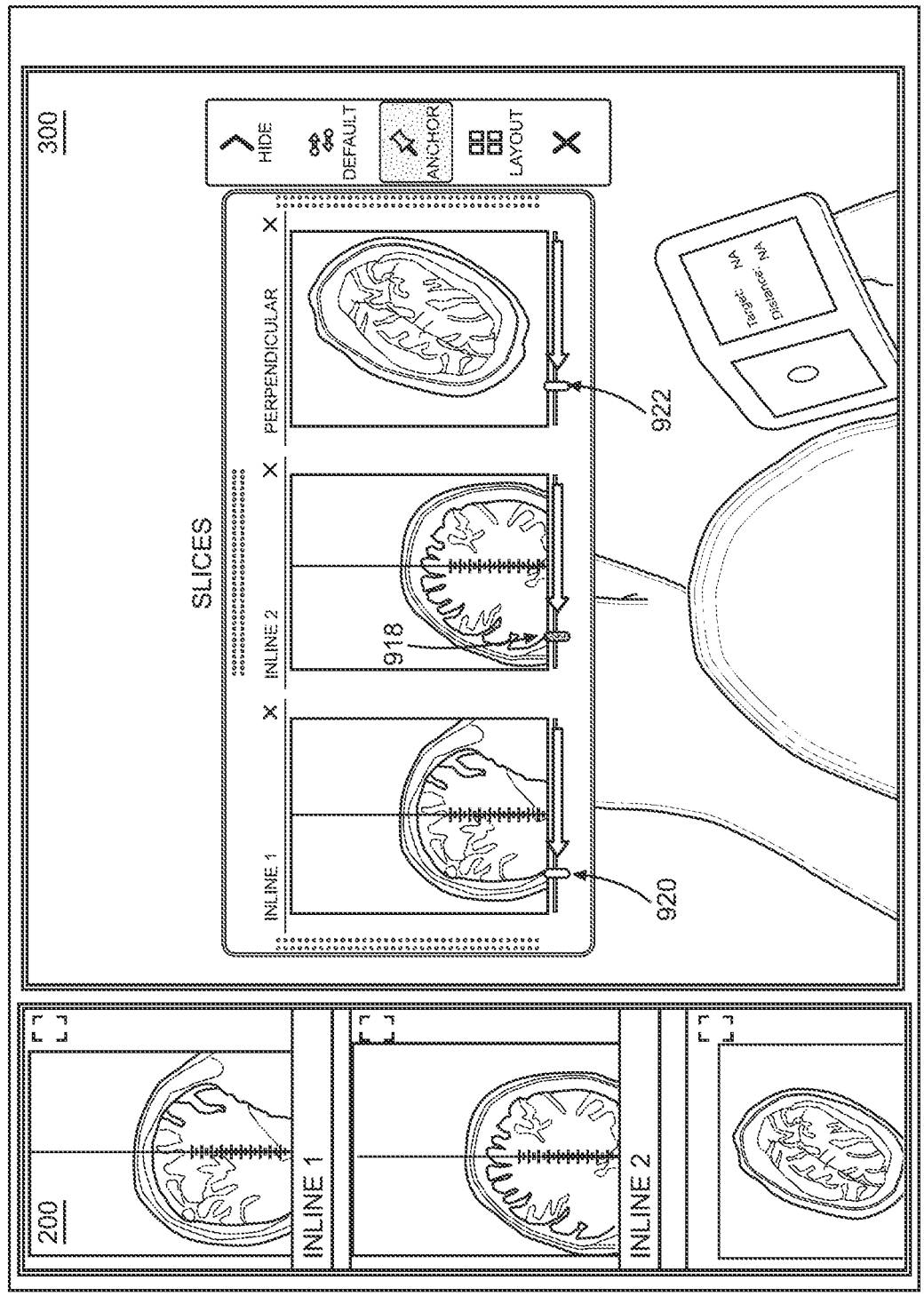

As shown in FIG. 9F, an embodiment(s) of the Interaction Engine may implement an inline slice scroll-bar virtual interaction while the inline mode is active. Each inline slice 900-1, 900-2, 900-3 may have a corresponding scroll-bar 918, 920, 922. As shown in FIG. 9G, the Interaction Engine may detect selection of a scroll-bar 918 and one or more subsequent detected and tracked physical gestures correspond to movement of the scroll-bar 918 either to the left or to the right. For example, movement of the scroll-bar 918 to the left results in execution of a zoom-out functionality to a display of the current slice layer in the second inline slice 900-2. Movement of the scroll-bar 918 to the right results in execution of a zoom-in functionality to the display of the current slice layer in the second inline slice 900-2.

In some embodiments, selection of the scroll-bar 918 implicitly includes selection of the other scroll-bars 920, 922. Movement resulting from the one or more physical gestures that correspond to the selected scroll-bar 918 will further be concurrently applied to the other scroll-bars 920, 922 such that the zoom-in and/or zoom-out functionalities are concurrently applied and portrayed in both the first inline slice 900-1 and the third inline slice 900-3.

Figure 10:
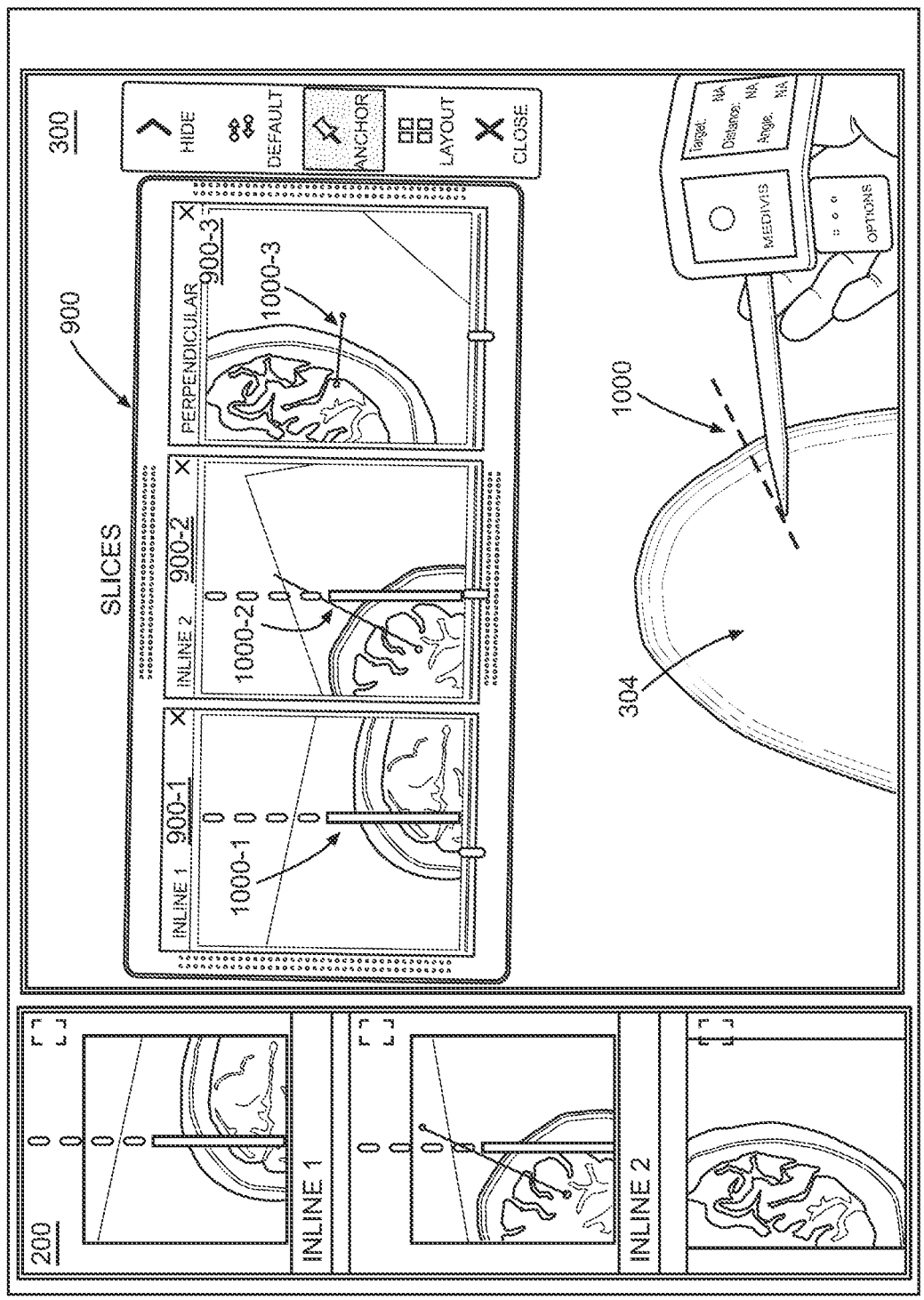
FIG. 10 is a diagram illustrating an exemplary environment in which some embodiments may operate.

As shown in FIG. 10, an embodiment(s) of the Interaction Engine may implement an inline slice trajectory virtual interaction while the inline mode is active. The inline view trajectory virtual interaction displays the instrument indicator as a central line in each inline slices 900-1, 900-2, 900-3. Each instrument indicator represents the pose of the instrument. According to various embodiments, the Interaction Engine modifies the AR display 300 to include display of a virtual trajectory 1000 (i.e. defined trajectory path) from an entry point in the medical model 304 to a target point in the medical model 304 projected on the plane that each slice is located.

For example, the virtual trajectory 1000 spans from a selected target point to a selected entry point. The virtual trajectory 1000 includes multiple sets of coordinates that occur between the selected target point and the selected entry point. Each set of coordinates along the virtual trajectory 1000 corresponds to a display position in the medical model 304. For example, each set of coordinates may be a display position with particular coordinates that reference a particular anatomical location represented by the medical model 304 that occurs along the displayed virtual trajectory 1000 and between the selected target and entry points.

The Interaction Engine further displays a first trajectory indicator 1000-1 concurrently with the centered first instrument indicator in the first inline view 900-1. The first trajectory indicator 1000-1 represents a pose of a planned trajectory 1000 with respect to the first portion of medical model data of the medical model 302 represented by the first inline slice 900-1. It is understood that, in FIG. 10, the first instrument indicator is displayed as overlayed upon the first trajectory indicator 1000-1 due to the current pose of the physical instrument being in alignment with the planned trajectory 1000 from the perspective of the first portion of medical model data of the medical model 302 represented by the first inline view 900-1.

The Interaction Engine further displays a second trajectory indicator 1000-2 concurrently with the centered second instrument indicator in the second inline slice 900-2. The second trajectory indicator 1000-2 represents a pose of the planned trajectory 1000 with respect to the second portion of medical model data of the medical model 302 represented by the second inline slice 900-2. The Interaction Engine displays a third trajectory indicator 1000-3 in the third inline slice (perpendicular slice), whereby the third trajectory indicator represents a pose of the defined trajectory path in the third portion of the 3D virtual medical.

According to various embodiments, the inline slice trajectory virtual interaction includes a trajectory focus virtual interaction. The Interaction Engine may update the center line of each respective each inline slice 900-1, 900-2, 900-3 to represent the trajectory indicators 1000-1, 1000-2, 1000-3. The respective instrument indicators may be concurrently displayed in the inline slices 900-1, 900-2, 900-3 in the trajectory focus virtual interaction as well. However, since the trajectory indicators 1000-1, 1000-2, 1000-3 are focused as the center lines in the views 900-1, 900-2, 900-3, the display position of each instrument indicators in the inline slices 900-1, 900-2, 900-3 will not be stationary.

State differently, where the fixed center lines of the inline slices 900-1, 900-2, 900-3 illustrated in FIG. 10 represent the instrument indicators and the trajectory indicators 1000-1, 1000-2, 1000-3 are concurrently displayed according to dynamic display positions responsive to detected and tracked changes represented by the instrument pose data, the trajectory focus virtual interaction reverses the display relationship. In the trajectory focus virtual interaction, trajectory indicators are the fixed center lines of the slices 900-1, 900-2, 900-3 and the instrument indicators are concurrently displayed according to dynamic display positions and orientations.

Figure 11:
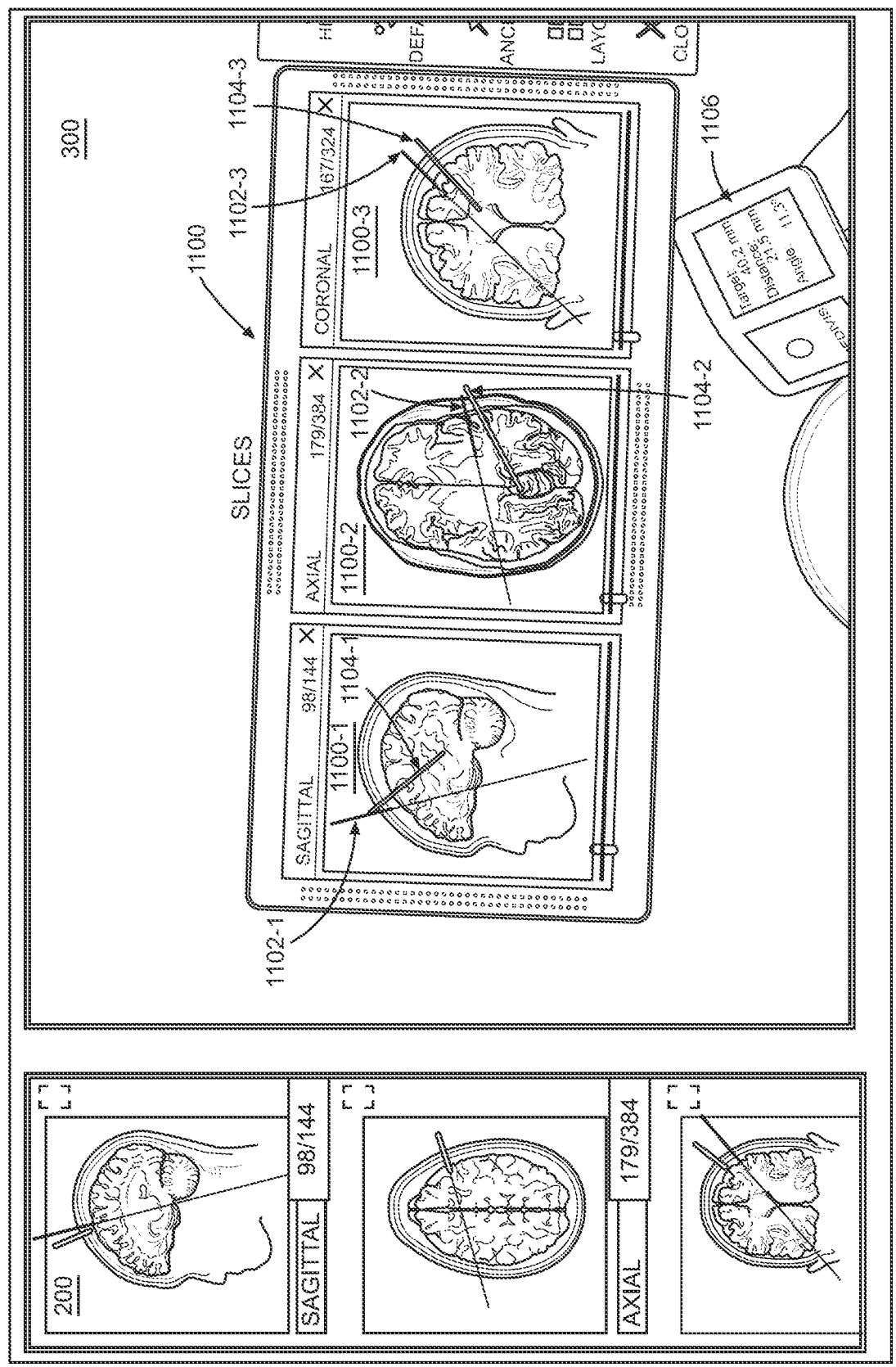
FIG. 11 is a diagram illustrating an exemplary environment in which some embodiments may operate.

As shown in FIG. 11, one or more embodiments of the Interaction Engine may include a axis view mode, also referred to projection view mode. In axis/projection view mode, the slice layer is parallel to the original coordinates of the 3D medical data. The Interaction Engine may implement a projection view virtual interaction while the axis mode is active. The Interaction Engine displays a projection panel 1100 with a sagittal slice 1100-1, an axial slice 1100-2 and a coronal slice 1100-3. The Interaction Engine further displays an instrument indicator 1102-1, 1102-1, 1102-3 and a trajectory indicator 1104-1, 1104-2, 1104-3 in each slice 1100-1, 1100-2, 1100-3. Each of the instrument indicators 1102-1, 1102-1, 1102-3 and trajectory indicators 1104-1, 1104-2, 1104-3 dynamic display positions responsive to detected and tracked changes represented by the instrument pose data.

Each slice 1100-1, 1100-2, 1100-3 portrays a portion(s) of medical model data that corresponds to a slice layer. The current slice layer for display in each slice 1100-1, 1100-2, 1100-3 is determined according to a current positional coordinate of a tip associated with the physical instrument 1106. For example, the tip may be a tip of the physical instrument 1106 or a tip of a virtual offset of the physical instrument 1106.

In various embodiments, the Interaction Engine determines the positional coordinates of the tip based on the current position and orientation of the physical instrument 1106. The Interaction Engine identifies medical model data that also currently maps to the tip's positional coordinates while the 3D virtual medical model 304 is at a current model pose. The Interaction Engine further identifies a slice layer number associated with the identified medical model data and renders medical model data from that slice layer in a slice 1100-1, 1100-2, 1100-3.

In various embodiments, the slice virtual interaction further includes a slice freeze virtual interaction. The slice freeze virtual interaction may be available in both the inline and projection modes. The Interaction Engine receives selection of a slice freeze functionality. In response to the selection of the slice freeze functionality, the Interaction Engine freezes the slice layers currently displayed in each of the slices 1100-1, 1100-2, 1100-3. However, the Interaction Engine continues to dynamically display the instrument indicators 1102-1, 1102-1, 1102-3 and trajectory indicators 1104-1, 1104-2, 1104-3 based on the current instrument pose data and to further overlay display of the instrument indicators 1102-1, 1102-1, 1102-3 and trajectory indicators 1104-1, 1104-2, 1104-3, at their respective updated display positions, over the frozen slices 1100-1, 1100-2, 1100-3.

Figure 12:
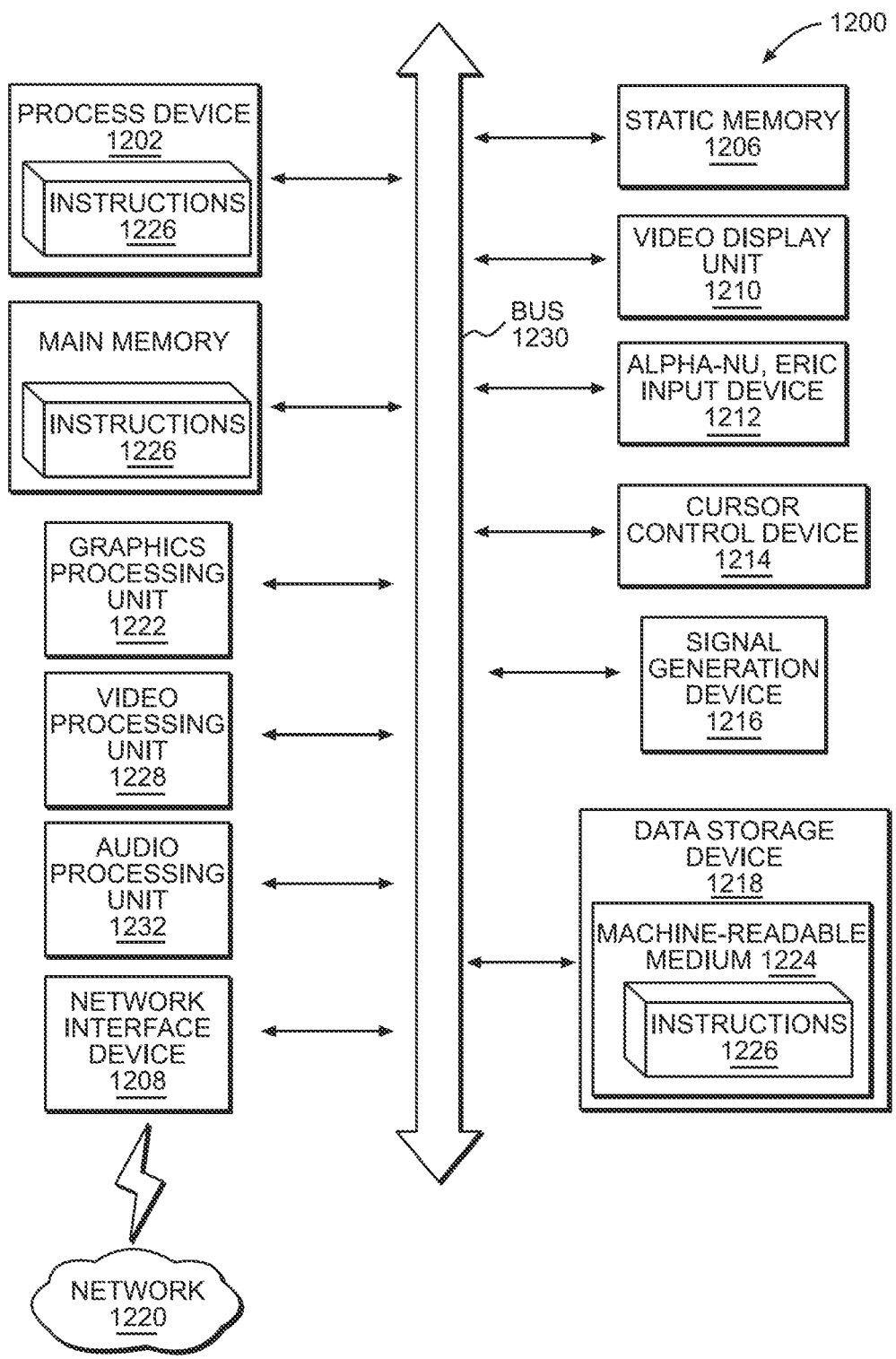
FIG. 12 is a diagram illustrating an exemplary environment in which some embodiments may operate.

FIG. 12 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 1200 includes a processing device 1202, a main memory 1204 (e.g., read-only memory (ROM), flash memory, dynamic random access memory (DRAM) such as synchronous DRAM (SDRAM) or Rambus DRAM (RDRAM), etc.), a static memory 1206 (e.g., flash memory, static random access memory (SRAM), etc.), and a data storage device 1218, which communicate with each other via a bus 1230.

Processing device 1202 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1202 may also be one or more special-purpose processing devices such as an application specific integrated circuit (ASIC), a field programmable gate array (FPGA), a digital signal processor (DSP), network processor, or the like. The processing device 1202 is configured to execute instructions 1226 for performing the operations and steps discussed herein.

The computer system 1200 may further include a network interface device 1208 to communicate over the network 1220. The computer system 1200 also may include a video display unit 1210 (e.g., a liquid crystal display (LCD) or a cathode ray tube (CRT)), an alphanumeric input device 1212 (e.g., a keyboard), a cursor control device 1214 (e.g., a mouse), a graphics processing unit 1222, a signal generation device 1216 (e.g., a speaker), graphics processing unit 1222, video processing unit 1228, and audio processing unit 1232.

The data storage device 1218 may include a machine-readable storage medium 1224 (also known as a computer-readable medium) on which is stored one or more sets of instructions or software 1226 embodying any one or more of the methodologies or functions described herein. The instructions 1226 may also reside, completely or at least partially, within the main memory 1204 and/or within the processing device 1202 during execution thereof by the computer system 1200, the main memory 1204 and the processing device 1202 also constituting machine-readable storage media.

In one implementation, the instructions 1226 include instructions to implement functionality corresponding to the components of a device to perform the disclosure herein. While the machine-readable storage medium 1224 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A computer-implemented method, comprising:
   generating within a unified three-dimensional (3D) coordinate space:
   (i) a 3D virtual medical model positioned according to a model pose; and
   (ii) at least one 3D virtual slice that corresponds with a view of respective slice layer from a plurality of slice layers associated with the 3D virtual medical model;
   rendering an Augmented Reality (AR) display that includes concurrent display of the 3D virtual medical model and the 3D virtual slice(s);
   detecting one or more physical gestures associated with at least one of a user and the physical instrument;
   identifying at least one interaction associated with the detected physical gestures;
   based on the identified interaction, determining a particular display position and orientation, in the unified 3D coordinate space, of a 3D virtual slice panel; and
   displaying the 3D virtual slice panel at the particular display position and orientation, the 3D virtual slice panel including display of the at least one 3D virtual slice.

2. The computer-implemented method of claim 1, wherein identifying at least one interaction comprises: identifying a slice panel selection interaction;
   prior to determining the display position and orientation of a 3D virtual slice panel:

determining a first display position and orientation, in the unified 3D coordinate space, of a 3D virtual menu based on the one or more physical gestures;

displaying the 3D virtual menu in the AR display at the first the display position and orientation;

detecting at least one subsequent physical gesture with respect to the 3D virtual menu, the at least one subsequent physical gesture corresponding to the identified interaction for the 3D virtual slice panel.

3. The computer-implemented method of claim 1, wherein identifying at least one interaction comprises: identifying a slice panel control interaction, further comprising:

identifying a selection of an anchor functionality from a 3D virtual slice panel menu adjacently displayed with a current display position of a 3D virtual slice panel;

wherein displaying the 3D virtual slice panel comprises:

maintaining display of a state of the 3D virtual slice panel present at the selection of the anchor functionality.

4. The computer-implemented method of claim 1, wherein detecting one or more physical gestures comprises: detecting a position and orientation of a physical instrument associated the one or more physical gestures;

wherein identifying at least one virtual interaction comprises:

identifying a physical instrument pose based on a current position and orientation of the physical instrument with respect to a current model pose;

defining a first plane perpendicular to a tubular body associated with the physical instrument pose;

defining a second plane parallel to the physical instrument tubular body;

defining a third plane parallel to the physical instrument tubular body and perpendicular to the second plane; and wherein displaying the 3D virtual slice panel comprises:

concurrently displaying a first slice, a second slice and a third slice in the 3D virtual slice panel;

(i) the first slice comprising a first portion of the 3D virtual medical model that maps to a current position, in the unified 3D coordinate space, on the first plane;

(ii) displaying a second slice comprising a second portion of the 3D virtual medical model that maps to respective positions, in the unified 3D coordinate space, on the second plane; and (iii) displaying a third slice comprising a third portion of the 3D virtual medical model that maps to respective positions, in the unified 3D coordinate space, on the third plane.

5. The computer-implemented method of claim 4, wherein identifying at least one interaction comprises further comprises:

identifying an inline view instrument virtual interaction, further comprising:

displaying, in the first slice, the first portion of the 3D virtual medical model with respect to a first instrument indicator based on the pose of the physical instrument; and displaying, in the second slice, the second portion of the 3D virtual medical model with respect to a second instrument indicator based on the pose of the physical instrument.

6. The computer-implemented method of claim 5, wherein identifying at least one interaction comprises further comprises:

identifying an inline view trajectory virtual interaction, further comprising:

displaying a first trajectory indicator concurrently with the first instrument indicator in the first slice, the first trajectory indicator representing a pose of a defined trajectory path in the first portion of the 3D virtual medical model;

displaying a second trajectory indicator concurrently with the second instrument indicator in the second slice, the second trajectory indicator representing a pose of the defined trajectory path in the second portion of the 3D virtual medical model; and displaying a third trajectory indicator in the third slice, the third trajectory indicator representing a pose of the defined trajectory path in the third portion of the 3D virtual medical model.

7. The computer-implemented method of claim 1, wherein identifying at least one virtual interaction comprises: identifying an axis view interaction, comprising:

identifying a physical instrument pose based on a current position and orientation of the physical instrument with respect to a current model pose;

and wherein displaying the 3D virtual slice panel comprises:

concurrently displaying a first axis slice, a second axis slice and a third axis slice in the 3D virtual slice panel;

(i) the first axis slice comprising a sagittal view of a first portion of the 3D virtual medical model that maps to a current first slice layer, the current first slice layer determined by a current position, in the unified 3D coordinate space, of a tip associated with the physical instrument;

(ii) the second axis slice comprising an axial view of a second portion of the 3D virtual medical model that maps to a current second slice layer, the current second slice layer determined by the current position of the tip associated with the physical instrument;

(iii) displaying a third axis slice comprising a coronal view of a third portion of the 3D virtual medical model that maps that maps to a current third slice layer, the current third slice layer determined by the current position of the tip associated with the physical instrument; and concurrently displaying an instrument indicator and a trajectory indicator in the first, second and third axis slices.

8. A system comprising one or more processors, and a non-transitory computer-readable medium including one or more sequences of instructions that, when executed by the one or more processors, cause the system to perform operations comprising:

generating within a unified three-dimensional (3D) coordinate space:

(i) a 3D virtual medical model positioned according to a model pose; and (ii) at least one 3D virtual slice that corresponds with a view of respective slice layer from a plurality of slice layers associated with the 3D virtual medical model;

rendering an Augmented Reality (AR) display that includes concurrent display of the 3D virtual medical model and the 3D virtual slice(s);

detecting one or more physical gestures associated with at least one of a user and the physical instrument;

identifying at least one interaction associated with the detected physical gestures;

based on the identified interaction, determining a particular display position and orientation, in the unified 3D coordinate space, of a 3D virtual slice panel; and displaying the 3D virtual slice panel at the particular display position and orientation, the 3D virtual slice panel including display of the at least one 3D virtual slice.

9. The system of claim 8, wherein identifying at least one interaction comprises: identifying a slice panel selection interaction;
prior to determining the display position and orientation of a 3D virtual slice panel:
determining a first display position and orientation, in the unified 3D coordinate space, of a 3D virtual menu based on the one or more physical gestures;
displaying the 3D virtual menu in the AR display at the first the display position and orientation;
detecting at least one subsequent physical gesture with respect to the 3D virtual menu, the at least one subsequent physical gesture corresponding to the identified interaction for the 3D virtual slice panel.

10. The system of claim 8, wherein identifying at least one interaction comprises: identifying a slice panel control interaction, further comprising:
identifying a selection of an anchor functionality from a 3D virtual slice panel menu adjacently displayed with a current display position of a 3D virtual slice panel, the 3D virtual slice panel including display of the at least one 3D virtual slice;
wherein displaying the 3D virtual slice panel comprises:
maintaining display of a state of the 3D virtual slice panel present at the selection of the anchor functionality.

11. The system of claim 8, wherein detecting one or more physical gestures comprises: detecting a position and orientation of a physical instrument associated the one or more physical gestures;
wherein identifying at least one virtual interaction comprises:
identifying a physical instrument pose based on a current position and orientation of the physical instrument with respect to a current model pose;
defining a first plane perpendicular to a tubular body associated with the physical instrument pose;
defining a second plane parallel to the physical instrument tubular body;
defining a third plane parallel to the physical instrument tubular body and perpendicular to the second plane; and
wherein displaying the 3D virtual slice panel comprises:
concurrently displaying a first slice, a second slice and a third slice in the 3D virtual slice panel;
(i) the first slice comprising a first portion of the 3D virtual medical model that maps to a current position, in the unified 3D coordinate space, on the first plane;
(ii) displaying a second slice comprising a second portion of the 3D virtual medical model that maps to respective positions, in the unified 3D coordinate space, on the second plane; and
(iii) displaying a third slice comprising a third portion of the 3D virtual medical model that maps to respective positions, in the unified 3D coordinate space, on the third plane.

12. The system of claim 11, wherein identifying at least one interaction comprises further comprises:
identifying an inline view instrument virtual interaction, further comprising:

displaying, in the first slice, the first portion of the 3D virtual medical model with respect to a first instrument indicator based on the pose of the physical instrument; and
displaying, in the second slice, the second portion of the 3D virtual medical model with respect to a second instrument indicator based on the pose of the physical instrument.

13. The system of claim 12, wherein identifying at least one interaction comprises further comprises:
identifying an inline view trajectory virtual interaction, further comprising:
displaying a first trajectory indicator concurrently with the first instrument indicator in the first slice, the first trajectory indicator representing a pose of a defined trajectory path in the first portion of the 3D virtual medical model;
displaying a second trajectory indicator concurrently with the second instrument indicator in the second slice, the second trajectory indicator representing a pose of the defined trajectory path in the second portion of the 3D virtual medical model; and
displaying a third trajectory indicator in the third slice, the third trajectory indicator representing a pose of the defined trajectory path in the third portion of the 3D virtual medical model.

14. The system of claim 8, wherein identifying at least one virtual interaction comprises: identifying an axis view interaction, comprising:
identifying a physical instrument pose based on a current position and orientation of the physical instrument with respect to a current model pose; and
wherein displaying the 3D virtual slice panel comprises:
concurrently displaying a first axis slice, a second axis slice and a third axis slice in the 3D virtual slice panel;
(i) the first axis slice comprising a sagittal view of a first portion of the 3D virtual medical model that maps to a current first slice layer, the current first slice layer determined by a current position, in the unified 3D coordinate space, of a tip associated with the physical instrument;
(ii) the second axis slice comprising an axial view of a second portion of the 3D virtual medical model that maps to a current second slice layer, the current second slice layer determined by the current position of the tip associated with the physical instrument;
(iii) displaying a third axis slice comprising a coronal view of a third portion of the 3D virtual medical model that maps that maps to a current third slice layer, the current third slice layer determined by the current position of the tip associated with the physical instrument; and
concurrently displaying an instrument indicator and a trajectory indicator in the first, second and third axis slices.

15. A computer program product comprising a non-transitory computer-readable medium having a computer-readable program code embodied therein to be executed by one or more processors, the program code including instructions for:
generating within a unified three-dimensional (3D) coordinate space:
(i) a 3D virtual medical model positioned according to a model pose; and
(ii) at least one 3D virtual slice that corresponds with a view of respective slice layer from a plurality of slice layers associated with the 3D virtual medical model;

rendering an Augmented Reality (AR) display that
  includes concurrent display of the 3D virtual medical
  model and the 3D virtual slice(s);
detecting one or more physical gestures associated with
  at least one of a user and the physical instrument;
identifying at least one interaction associated with the
  detected physical gestures;
based on the identified interaction, determining a par-
  ticular display position and orientation, in the unified
  3D coordinate space, of a 3D virtual slice panel; and
displaying the 3D virtual slice panel at the particular
  display position and orientation, the 3D virtual slice
  panel including display of the at least one 3D virtual
  slice.

16. The computer program product of claim 15, wherein identifying at least one interaction comprises: identifying a slice panel selection interaction;
  prior to determining the display position and orientation of a 3D virtual slice panel:
    determining a first display position and orientation, in the unified 3D coordinate space, of a 3D virtual menu based on the one or more physical gestures;
    displaying the 3D virtual menu in the AR display at the first the display position and orientation;
    detecting at least one subsequent physical gesture with respect to the 3D virtual menu, the at least one subsequent physical gesture corresponding to the identified interaction for the 3D virtual slice panel.

17. The computer program product of claim 15, wherein identifying at least one interaction comprises: identifying a slice panel control interaction, further comprising:
  identifying a selection of an anchor functionality from a 3D virtual slice panel menu adjacently displayed with a current display position of a 3D virtual slice panel, the 3D virtual slice panel including display of the at least one 3D virtual slice;
  wherein displaying the 3D virtual slice panel comprises:
    maintaining display of a state of the 3D virtual slice panel present at the selection of the anchor functionality.

18. The computer program product of claim 15, wherein detecting one or more physical gestures comprises: detecting a position and orientation of a physical instrument associated the one or more physical gestures;
  wherein identifying at least one virtual interaction comprises:
    identifying a physical instrument pose based on a current position and orientation of the physical instrument with respect to a current model pose;
    defining a first plane perpendicular to a tubular body associated with the physical instrument pose;
    defining a second plane parallel to the physical instrument tubular body;
    defining a third plane parallel to the physical instrument tubular body and perpendicular to the second plane; and
  wherein displaying the 3D virtual slice panel comprises:
    concurrently displaying a first slice, a second slice and a third slice in the 3D virtual slice panel;
      (i) the first slice comprising a first portion of the 3D virtual medical model that maps to a current position, in the unified 3D coordinate space, on the first plane;
      (ii) displaying a second slice comprising a second portion of the 3D virtual medical model that maps to respective positions, in the unified 3D coordinate space, on the second plane; and
      (iii) displaying a third slice comprising a third portion of the 3D virtual medical model that maps to respective positions, in the unified 3D coordinate space, on the third plane.

19. The computer program product of claim 18, wherein identifying at least one interaction comprises further comprises:
  identifying an inline view instrument virtual interaction, further comprising:
    displaying, in the first slice, the first portion of the 3D virtual medical model with respect to a first instrument indicator based on the pose of the physical instrument; and
    displaying, in the second slice, the second portion of the 3D virtual medical model with respect to a second instrument indicator based on the pose of the physical instrument.

20. The computer program product of claim 19, wherein identifying at least one interaction comprises further comprises:
  identifying an inline view trajectory virtual interaction, further comprising:
    displaying a first trajectory indicator concurrently with the first instrument indicator in the first slice, the first trajectory indicator representing a pose of a defined trajectory path in the first portion of the 3D virtual medical model;
    displaying a second trajectory indicator concurrently with the second instrument indicator in the second slice, the second trajectory indicator representing a pose of the defined trajectory path in the second portion of the 3D virtual medical model; and
    displaying a third trajectory indicator in the third slice, the third trajectory indicator representing a pose of the defined trajectory path in the third portion of the 3D virtual medical model.

* * * * *